US006255082B1

(12) United States Patent
Lizardi

(10) Patent No.: US 6,255,082 B1
(45) Date of Patent: Jul. 3, 2001

(54) ARTIFICIAL LONG TERMINAL REPEAT VECTORS

(75) Inventor: Paul M. Lizardi, Hamden, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/396,340

(22) Filed: Sep. 15, 1999

Related U.S. Application Data

(60) Provisional application No. 60/100,305, filed on Sep. 15, 1998.

(51) Int. Cl.$^7$ .................................................. C12P 19/34
(52) U.S. Cl. ...................... 435/91.1; 435/91.1; 435/91.2; 435/5; 435/6; 536/23.1; 536/24.3; 536/24.32; 536/24.33; 536/24.5
(58) Field of Search .................................. 435/91.1, 6, 5, 435/91.2; 536/24.5, 24.3, 24.32, 24.33, 23.1

(56) References Cited

U.S. PATENT DOCUMENTS

| | | |
|---|---|---|
| 4,748,111 | 5/1988 | Dattagupat et al. . |
| 4,883,750 | 11/1989 | Whiteley et al. . |
| 4,965,188 | 10/1990 | Mullis et al. . |
| 4,994,373 | 2/1991 | Stavrianopoulos et al. . |
| 5,001,050 | 3/1991 | Blanco et al. . |
| 5,043,272 | 8/1991 | Hartley . |
| 5,130,238 | 7/1992 | Malek et al. . |
| 5,198,543 | 3/1993 | Blanco et al. . |
| 5,242,794 | 9/1993 | Norman et al. . |
| 5,273,638 | 12/1993 | Konrad et al. . |
| 5,328,824 | 7/1994 | Ward et al. . |
| 5,354,668 | 10/1994 | Auerbach . |
| 5,409,818 | 4/1995 | Davey et al. . |
| 5,412,087 | 5/1995 | McGall et al. . |
| 5,427,930 | 6/1995 | Birkenmeyer et al. . |
| 5,429,807 | 7/1995 | Matson et al. . |
| 5,455,166 | 10/1995 | Walker . |
| 5,510,270 | 4/1996 | Fodor et al. . |
| 5,521,065 | 5/1996 | Whiteley et al. . |
| 5,547,843 | 8/1996 | Studier et al. . |
| 5,591,609 | 1/1997 | Auerbach . |
| 5,614,389 | 3/1997 | Auerbach . |
| 5,614,390 | 3/1997 | McCaslin et al. . |
| 5,629,158 | 5/1997 | Uhlen . |
| 5,629,179 | 5/1997 | Mierendorf et al. . |
| 5,714,320 | 2/1998 | Kool . |
| 5,733,733 | 3/1998 | Auerbach . |
| 5,854,033 | 12/1998 | Lizardi . |

FOREIGN PATENT DOCUMENTS

| | | |
|---|---|---|
| 84173/91 | 2/1992 | (AU) . |
| 0128 332 | 12/1984 | (EP) . |
| 0356 021 | 7/1989 | (EP) . |
| 0466 520 | 1/1992 | (EP) . |
| 0505 012 | 9/1992 | (EP) . |
| 0 640 691 | 3/1995 | (EP) . |
| 0667 393 | 8/1995 | (EP) . |
| 0678 582 | 10/1995 | (EP) . |
| 0439 182 | 4/1996 | (EP) . |
| 4-262799 | 9/1992 | (JP) . |
| 4-304900 | 10/1992 | (JP) . |
| WO 91/08307 | 6/1991 | (WO) . |
| WO 92/01813 | 2/1992 | (WO) . |
| WO 94/24312 | 10/1994 | (WO) . |
| WO 95/03430 | 2/1995 | (WO) . |
| WO 95/03432 | 2/1995 | (WO) . |
| WO 95/22623 | 8/1995 | (WO) . |
| WO 95/25180 | 9/1995 | (WO) . |
| WO 95/35390 | 12/1995 | (WO) . |
| WO 96/00795 | 1/1996 | (WO) . |
| WO 96/33207 | 10/1996 | (WO) . |
| WO 97/19193 | 5/1997 | (WO) . |
| WO 97/20948 | 6/1997 | (WO) . |
| WO 97/42346 | 11/1997 | (WO) . |
| WO 98/39485 | 9/1998 | (WO) . |

OTHER PUBLICATIONS

Abravaya, et al., "Detection of point mutations with a modified ligase chain reaction (Gap–LCR)," *Nucleic Acids Res.* 23(4):675–682 (1995).

Aliotta, et al., "Thermostable Bst DNA polymerase I lacks a 3'–>5' proofreading exonuclease activity," *Genet Anal.* 12(5–6):185–95 (1996).

Alves & Carr, "Dot blot detection of point mutations with adjacently hybridising synthetic oligonucleotide probes," *Nucl. Acids. Res.* 16:8723 (1988).

Arnold, et al., "Assay Formats Involving Acridinium–Ester–Labeled DNA Probes," *Clin. Chem.* 35(8): 1588–1594 (1989).

(List continued on next page.)

Primary Examiner—W. Gary Jones
Assistant Examiner—Janell E. Taylor
(74) Attorney, Agent, or Firm—Needle & Rosenberg, P.C.

(57) ABSTRACT

Disclosed are compositions and an in vitro method for cloning and/or amplification of nucleic acid sequences of interest. The method is based on strand displacement replication of the nucleic acid sequences by multiple priming on artificial long terminal repeat (ALTR) sequences appended to the ends of the nucleic acid molecule of interest. The nucleic acid molecules for cloning and amplification can be very long, up to 40 to 80 Kb or longer. In a preferred form of the method, a single primer is used to prime strand displacement replication at multiple sites in artificial long terminal repeat sequences, flanking a target nucleic acid, containing multiple tandem repeats of a primer complement sequence. Amplification proceeds by replication initiated at each primer and continuing through the target nucleic acid sequence. This nested replication of multiple copies significantly increases the amplification yield for extremely long nucleic acid molecules. By using a sufficient number of repeat units in the ALTRs, only a few rounds of replication are required to produce hundreds of thousands of copies of the nucleic acid sequence of interest. A preferred form of the disclosed method makes use of indexed artificial long terminal repeats that allow amplification and identification of specific nucleic acid fragments present in a mixture of nucleic acid fragments without requiring any knowledge of the sequence of the nucleic acid fragment.

25 Claims, 3 Drawing Sheets

OTHER PUBLICATIONS

Barany, "Genetic disease detection and DNA amplification using cloned thermostable ligase," *Proc. Natl. Acad Sci. USA* 88: 189–193 (1991).

Bertina, et al., "Mutation in blood coagulation factor V associated with resistance to activated protein C", *Nature* 369: 64–67 (1994).

Birkenmeyer & Mushahwar, "DNA probe amplification methods," *Journal of Virological Methods* 35:117–126 (1991).

Blanco & Salas, "Characterization and purification of a phage ø29–encoded DNA polymerase required for the initiation of replication," *Proc. Natl. Acad. Sci.* 81:5325–5329 (1984).

Blanco, et al., "Highly Efficient DNA Synthesis by the Phage ø29 DNA Polymerase," *Journal of Biological Chemistry* 264(15):8935–8940 (1989).

Blanco, et al., "Terminal protein–primed DNA amplification," *Proc. Natl. Acad. Sci.* 91:12198–202 (1994).

Boehmer & Lehman, "Herpes Simplex Virus Type 1 ICP8: Helix–Destabilizing Properties," *Journal of Virology* 67(2):711–715 (1993).

Broude, et al., "Enhanced DNA sequencing by hybridization," *Proc. Natl. Acad. Sci.* 91:3072–76 (1994).

Burgess & Jacutin, "A new photolabile protecting group for nucleotides," *Am. Chem Soc. Abstracts*, vol. 221, abstract 281 (1996).

Butler & Chamberlin, "Bacteriophage SP6–specific RNA Polymerase," *Journal of Biological Chemistry* 257:5772–5778 (1982).

Chatterjee, et al., "Cloning and overexpression of the gene encoding bacteriophage T5 DNA polymerase," *Gene* 97:13–19 (1991).

Chetverina & Chetverin, "Cloning of RNA molecules in vitro," *Nucl. Acids. Res.* 21:2349–53 (1993).

Daubendiek & Kool, "Generation of catalytic RNAs by rolling transcription of synthetic DNA nanocircles," *Nat Biotechnol.* 15(3):273–7 (1997).

Daubendiek, et al., "Rolling–circle RNA synthesis: Circular oligonucleotides as efficient substrates for T7 RNA polymerase," *J. Am. Chem. Soc.* 117:7818–19 (1995).

Davanloo, et al., "Cloning and expression of the gene for bacteriophage T7 RNA polymerase," *Proc. Natl. Acad. Sci. USA* 81:2035–2039 (1984).

Davis, et al., *Advanced Bacterial Genetics—A Manual for Genetic Engineering* (Cold Spring Harbor Laboratory, Cold Spring Harbor, N.Y., 1980).

Dynal, *Biomagnetic Techniques in Molecular Biology*, 1995.

Ernst, et al., "Cyanine dye labeling reagents for sulfhydryl groups," *Cytometry* 10:3–10 (1989).

Fire & Xu, "Rolling replication of short DNA circles," *Proc. Natl. Acad Sci. USA* 92:4641–4645 (1995).

Gasparro, et al., "Site–specific targeting of psoralen photoadducts with a triple helix–forming oligonucleotide: characterization of psoralen monoadduct and crosslink formation," *Nucleic Acids Research* 22(14):2845–2852 (1994).

Gerdes, et al., "Dynamic changes in the higher–level chromatin organization of specific sequences revealed by in situ hybridization to nuclear halos," *J Cell Biol.* 126(2):289–304 (1994).

Gunji, et al., "Correlation Between the Serum Level of Hepatitis C Virus RNA and Disease Activities in Acute and Chronic Hepatitis C," *Int. J. Cancer* 52(5):726–730 (1992).

Guo, et al., "Direct fluorescence analysis of genetic polymorphisms by hybridization with oligonucleotide arrays on glass supports," *Nucleic Acids Res.* 22(24):5456–5465 (1994).

Guo, et al., "Enhanced discrimination of single nucleotide polymorphisms by artificial mismatch hybridization," *Nature Biotechnology* 15:331–335 (1997).

Gupta, et al., "Expression of HIV–1 RNA in plasma correlates with the development of AIDS: A multicenter AIDS cohort study," *Ninth International Conference on AIDS/Fourth STD World Congress* Jun. 6–11, 1993, Berlin, Germany.

Hacia, et al., "Detection of heterozygous mutations in BRCA1 using high density oligonucleotide arrays and two––color fluorescence analysis," *Nature Genetics* 14:441–447.

Hagiwara, et al., "Quantitation of hepatitis C Virus RNA in Serum of Asymptomatic Blood Donors and Patients with Type C Chronic Liver Disease," *Hepatology* 17(4):545–550 (1993).

Hanvey, et al., "Antisense and Antigene Properties of Peptide Nucleic Acids," *Science* 258: 1481–1485 (1992).

Hata, et al., "Structure of the Human Ornithine Transcarbamylase Gene," *J. Biochem.* 103: 302–308 (1988).

Hendrickson, et al., "High sensitivity multianalyte immunoassay using covalent DNA–labeled antibodies and polymerase chain reaction," *Nucleic Acids Res.* 23(3):522–529 (1995).

Hermanson, et al., eds., *Immobilized Affinity Ligands*, (Academic Press, New York, 1992).

Holloway, et al., "An exonuclease–amplification coupled capture technique improves detection of PCR product," *Nucleic Acids Research* 21:3905–3906 (1993).

Hoy, et al., "Bromodeoxyuridine/DNA analysis of replication in CHO cells after exposure to UV light," *Mutation Research* 290:217–230 (1993).

Hsuih, et al., "Quantitative Detection of HCV RNA Using Novel Ligation–Dependent Polymerase Chain Reaction", *American Association for the Study of Liver Diseases*, (Chicago, IL, Nov. 3–7, 1995) [poster abstract].

Itakura, et al., "Synthesis and Use of Synthetic Oligonucleotides," *Annual Review of Biochemistry* 53:323–356 (1984).

Jacobsen, et al., "The N–Terminal Amino–Acid Sequences of DNA Polymerase I from *Escherichia coli* and of the Large and the Small Fragments Obtained by a Limited Proteolysis," *Eur. J. Biochem.* 45:623–627 (1974).

Jiang, et al., "An efficient method for generation and subcloning of tandemly repeated DNA sequences with defined length, orientation and spacing," *Nucl. Acids Res.* 24:3278–3279 (1996).

Johnstone & Thorpe, *Immunochemistry In Practice* (Blackwell Scientific Publications, Oxford, England, 1987) pp. 209–216 and 241–242.

Jónsson, et al., "Sequence of the DNA ligase–encoding gene from *Thermus scotoductus* and conserved motifs in DNA ligases," *Gene* 151(1&2):177–180 (1995).

Jung, et al., "Bacteriophage PRDI DNA polymerase: Evolution of DNA polymerases," *Proc. Natl. Acad. Sci. USA* 84:8287 (1987).

Kaboord & Benkovic, "Accessory proteins function as matchmakers in the assembly of the T4 DNA polymerase holoenzyme," *Current Biology* 5: 149–157 (1995).

Kälin, et al., "Evaluation of the ligase chain reaction (LCR) for the detection of point mutations," *Mutation Research* 283(2): 119–123 (1992).

Kaplan, et al., "Rapid photolytic release of adenosine 5'–triphosphate from a protected analogue: utilization by the Na:K pump of human red blood cell ghosts" *Biochem.* 17:1929–1935 (1978).

Kellogg, et al., "TaqStart Antibody™: "Hot Start" PCR Facilitated by a Neutralizing Monoclonal Antibody Directed Against Taq DNA Polymerase," *Bio Techniques* 16(6):1134–1137 (1994).

Kerkhof, "A Comparison of Substrates for Quantifying the Signal from a Nonradiolabeled DNA Probe," *Analytical Biochemistry* 205:359–364 (1992).

Kong, et al., "Characterization of a DNA Polymerase from the Hyperthermophile Archaea *Thermococcus litoralis*," *Journal of Biological Chemistry* 268:1965–1975 (1993).

Kool, et al., "Circular oligonucleotides: New concepts in oligonucleotide design," *Annu. Rev. Biophys. Biomol. Struct.* 25:1–28 (1996).

Kunkel, et al., "Rapid and Efficient Site–Specific Mutagenesis without Phenotypic Selection," *Methods in Enzymology* 154: 367–382 (1987).

Lamture, et al., "Direct detection of nucleic acid hybridization on the surface of a charge coupled device," *Nucl. Acids Res.* 22:2121–25 (1994).

Landegren, "Molecular mechanics of nucleic acid sequence amplification," *Trends Genetics* 9:199–202 (1993).

Landegren, et al., "A Ligase–Mediated Gene Detection Technique," *Science* 241:1077–1080 (1988).

Langer, et al., "Enzymatic synthesis of biotin–labeled polynucleotides: Novel nucleic acid affinity probes", *Proc. Natl. Acad. Sci. USA* 78(11):6633–6637 (1981).

Lawyer, et al., "High–level Expression, Purification, and Enzymatic Characterization of Full–length *Thermus aquaticus* DNA Polymerase and Truncated Form Deficient in 5' to 3' Exonuclease Activity," *PCR Methods Applications* 2(4): 275–287 (1993).

Lee, et al., "Coordinated leading and lagging strand DNA synthesis on a minicircular template," *Mol. Cell.* 1(7):1001–10 (1998).

Lefrere, et al., "Towards a new predictor of AIDS progression through the quantitation of HIV–1 DNA copies by PCR in HIV–infected individuals," *British Journal of Haematology* 82(2): 467–471 (1992).

Lesnik & Freier, "Relative Thermodynamic Stability of DNA, RNA and DNA:RNA Hybrid Duplexes: Relationship with Base Composition and Structure," *Biochemistry* 34: 10807–10815 (1995).

Liu, et al., "Rolling circle DNA synthesis: Small circular oligonucleotides as efficient templates for DNA polymerases," *J. Am. Chem. Soc.* 118:1587–1594 (1996).

Lizardi, et al., "Cascade rolling circle amplification, a homogeneous fluorescence detection system for DNA diagnostics," *Clin. Chem.* 43: 2219–20 (1997).

Lizardi, et al., "Mutation detection and single–molecule counting using isothermal rolling–circle amplification," *Nat Genet.* 19(3):225–32 (1998).

Lockhart, et al., "Expression monitoring by hybridization to high–density oligonucleotide arrays," *Nature Biotechnology* 14:1675–1680 (1996).

Lu, et al., "High Concentration of Peripheral Blood Mononuclear Cells Harboring Infectious Virus Correlates with Rapid Progression of Human Immunodeficiency Virus Type 1–Related Diseases," *JID* 168(5):1165–8116 (1993).

Lukyanov, et al., "Molecule by molecule PCR amplification of complex DNA mixtures for direct sequencing: an approach to in vitro cloning," *Nucleic Acids Res.* 24(11):2194–5 (1996).

Luo, et al., "Improving the fidelity of *Thermus thermophilus* DNA ligase," *Nucl. Acids Res.* 24:3071–3078 (1996).

Marshall, et al., "Detection of HCV RNA by the asymmetric gap ligase chain reaction," *PCR Methods Appl.* 4(2):80–4 (1994).

Maskos, et al., "Oligonucleotide hybridizations on glass supports: a novel linker for oligonucleotides synthesized in situ," *Nucleic Acids Research* 20:1679–1684 (1992).

Matsumoto, et al., "Primary structure of bacteriophage M2 DNA polymerase: conserved segments within protein–priming DNA polymerases and DNA polymerase I of *Escherichia coli*," *Gene* 84(2): 247–255 (1989).

McCray, et al., "A new approach to time–resolved studies of ATP–requiring biological systems: Laser flash photolysis of caged ATP," *Proc. Natl. Acad. Sci. USA* 77:7237–7241 (1980).

McGraw, et al., "Sequence–dependant olkgonucleotide–target duplex stabilities: rules from empirical studies with a set of twenty–mers," *Biotechniques* 8:674–678 (1990).

Melton, et al., "Efficient in vitro synthesis of biologically active RNA and RNA hybridization probes from plasmids containing a bacteriophage SP6 promoter," *Nucleic Acids Res.* 12(18):7035–56 (1984).

Metzker, et al., "Termination of DNA synthesis by novel 3'–modified–deoxyribonucleoside 5'–triphosphates" *Nucleic Acids Research* 22:4259–4267 (1994).

Mujumdar, et al., "Cyanine dye labeling reagents containing isothiocyanate groups" *Cytometry* 10:11–19 (1989).

Narang, et al., "Chemical Synthesis of Deoxyoligonucleotides by the Modified Triester Method", *Methods Enzymology* 65:610–620 (1980).

Newton, et al., "Analysis of any point mutation in DNA. The amplification refractory mutation system (ARMS)," *Nucleic Acids Res.* 17(7):2503–16 (1989).

Nielsen, et al., "Peptide Nucleic Acid (PNA). A DNA Mimic with a Peptide Backbone," *Bioconjugate Chemistry*, 5: 3–7 (1994).

Nielsen, et al., "Peptide nucleic acids (PNAs): Potential anti–sense and anti–gene agents," *Anti–Cancer Drug Design*, 8: 53–63 (1993).

Nikiforov, et al., "Genetic Bit Analysis: a solid phase method for typing single nucleotide polymorphisms," *Nucleic Acids Res.* 22(20):4167–75 (1994).

Nikiforov, et al., "The Use of Phosphorothioate Primers and Exonuclease Hydrolysis for the Preparation of Single–stranded PCR Products and their Detection by Solid––phase Hybridization," *PCR Methods and Applications* 3: 285–291 (1994).

Nilsson, et al., "Padlock Probes: Circularizing Oligonucleotides for Localized DNA Detection," *Science* 265: 2085–2088 (1994).

Nilsson, et al., "Padlock probes reveal single–nucleotide differences, parent of origin and in situ distribution of centromeric sequences in human chromosomes 13 and 21," *Nat Genet.* 16(3):252–5 (1997).

Ørum, et al., "Single base pair mutation analysis by PNA directed PCR clamping," *Nucleic Acids Research* 21(23):5332–5336 (1993).

Panasenko, et al., "A Simple, Three–Step Procedure for the Large Scale Purification of DNA Ligase from a Hybrid λ Lysogen Construction in Vitro," *Journal Biological Chemistry* 253:4590–4592 (1978).

Parker, et al., "Targeted gene walkin polymerase chain reaction," *Nucl. Acids Res.* 19:3055–60 (1991).

Pease, et al., "Light–generated oligonucleotide arrays for rapid DNA sequence analysis," *Proc. Natl. Acad. Sci. USA* 91(11):5022–5026 (1994).

Piatak, et al., "High Levels of HIV–1 in Plasma During All Stages of Infection Determined by Competitive PCR," *Science* 259(5102):1749–1754 (1993).

Pillai, et al., "Photoremovable protecting groups in organic synthesis," *Synthesis* 1–26 (1980).

Pokrovskaya & Gurevich, "In vitro transcription: preparative RNA yields in analytical scale reactions," *Anal Biochem.* 220(2):420–3 (1994).

Prakash & Kool, "Structural effects in the recognition of DNA by circular oligonucleotides," *J. Amer. Chem. Soc.* 114:3523–3527 (1992).

Ramsing, et al., "Helix–coil transition of parallel–stranded DNA. Thermodynamics of hairpin and linear duplex oligonucleotides," *Biochem.* 28:9528–9535 (1989).

Richards, et al., "Conditional mutator phenotypes in hMS2H2–deficient tumor cell lines," *Science* 277:1523–1526 (1997).

Ried, et al., "Simultaneous visualization of seven different DNA probes by in situ hybridization using combinatorial fluorescence and digital imaging microscopy," *Proc Natl Acad Sci U S A.* 89(4):1388–92 (1992).

Rigler & Romano, "Differences in the Mechanism of Stimulation of T7 DNA Polymerase by Two Binding Modes of *Escherichia coli* Single–stranded DNA–binding Protein," *Journal of Biological Chemistry*, 270(15): 8910–8919 (1995).

Rychlik, et al., "Optimization of the annealing temperature for DNA amplification in vitro," *Nucleic Acids Research* 18(21): 6409–6412 (1990).

Rys & Persing, "Preventing false positives: quantitative evaluation of three protocols for inactivation of polymerase chain reaction amplification products," *J Clin Microbiol.* 31(9):2356–60 (1993).

Saksela, et al., "Human immunodeficiency virus type 1 mRNA expression in peripheral blood cells predicts disease progression independently of the numbers of CD4+ lymphocytes," *Proc. Natl. Acad. Sci. USA* 91(3): 1104–1108 (1994).

Sambrook, et al., "Molecular Cloning: A Laboratory Manual, Second Edition" (Chapters 5, 6), *Cold Spring Harbor Laboratory Press*, Cold Spring Harbor, N.Y., 1989.

Saris, et al., "Blotting of RNA onto ion exchange paper allowing subsequent characterization by in situ translation in addition to blot hybridization," *Nucleic Acids Res.* 10(16):4831–43 (1982).

Schena, et al., "Quantitative Monitoring of Gene Expression Patterns with a Complementary DNA Microarray," *Science* 270:467–470 (1995).

Schena, et al., "Parallel human genome analysis: Microarray–based expression monitoring of 1000 genes," *Proc. Natl. Acad. Sci. USA* 91:10614–10619 (1994).

Schenborn & Meirendorf, "A novel transcription property of SP6 and 17 RNA polymerases: dependence on template structure," *Nucleic Acids Research* 13(17):6223–6236 (1985).

Schwarz, et al., "Improved yields of long PCR products using gene 32 protein," *Nucl. Acid Res.* 18:1079 (1989).

Siegal, et al., "A Novel DNA Helicase from Calf Thymus," *Journal of Biological Chemistry* 267(19): 13629–13635 (1992).

Skaliter & Lehman, "Rolling circle DNA replication in vitro by a complex of herpes simplex virus type 1–encoded enzymes," *Proc. Natl. Acad. Sci. USA* 91(22):10665–10669 (1994).

Speicher, et al., "Karyotyping human chromosomes by combinatorial multi–fluor FISH," *Nature Genetics* 12(4): 368–375 (1996).

Stimpson, et al., "Real–time detection of DNA hybridization and melting on oligonucleotide arrays by using optical wave guides," *Proc. Natl. Acad. Sci. USA* 92(14):6379–6383 (1995).

Strauss & Jacobowitz, "Quantitative measurement of calretinin and beta–actin mRNA [correction of mRNAIN] in rat brain micropunches without prior isolation of RNA," *Mol Brain Res.* 20(3):229–39 (1993).

Strong, et al., "Marked improvement of PAC and BAC cloning is achieved using electroelution of pulsed–field gel–separated partial digests of genomic DNA," *Nucleic Acids Res.* 25(19):3959–61 (1997).

Studier, et al., "Use of T7 RNA Polymerase to Direct Expression of Cloned Genes," *Methods of Enzymology* 185: 60–89 (1990).

Syvänen, et al., "Fast quantification of nucleic acid hybrids by affinity–based hybrid collection," *Nucleic Acids Res.* 14(12):5037–48 (1986).

Tabor & Richardson, "Selective inactivation of the exonuclease activity of bacteriophage T7 DNA polymerase by in vitro mutagenesis," *J. Biol. Chem.* 264:6447–6458 (1989).

Tabor & Richardson, "Selective oxidation of the exonuclease domain of bacteriophage T7 DNA polymerase," *J. Biol. Chem.* 262:15330–15333 (1987).

Taylor, ed, *Protein immobilization: fundamentals and applications* (M. Dekker, New York, 1991).

Tsurumi, et al., "Functional Interaction between Epstein-–Barr Virus DNA Polymerase Catalytic Subunit and Its Accessory Subunit In Vitro," *Journal of Virology* 67(12):7648–7653 (1993).

Tyagi & Kramer, "Molecular beacons: probes that fluoresce upon hybridization," *Nature Biotechnology* 14:303–308 (1996).

Velculescu, et al., "Serial analysis of gene expression," *Science.* 270(5235):484–7 (1995).

Villemain & Giedroc, "The N–terminal B–domain of T4 gene 32 protein modulates the lifetime of cooperatively bound Gp32–ss nucleic acid complexes," *Biochemistry.* 35(45):14395–404 (1996).

Vogelstein, et al., "Supercoiled loops and eucaryotic DNA replicaton," *Cell.* 22(1 Pt 1):79–85 (1980).

Waggoner, "Covalent labeling of proteins and nucleic acids with fluorophores," *Meth. Enzymology* 246:362–373 (1995).

Walker & Linn, "Detection of *Mycobacterium tuberculosis* DNA with thermophilic strand displacement amplification and fluorescence polarization," *Clin Chem.* 42(10):1604–8 (1996).

Walker, et al., "Strand displacement amplification—an isothermal, in vitro DNA amplification technique," *Nucleic Acids Res.* 20(7):1691–6 (1992).

Walter & Strunk, "Strand displacement amplification as an in vitro model for rolling–circle replication: deletion formation and evolution during serial transfer," *Proc Natl Acad Sci U S A*. 91(17):7937–41 (1994).

Wansink, et al., "Fluorescent Labeling of Nascent RNA Reveals Transcription by RNA Polymerase II in Domains Scattered Throughout the Nucleus," *Journal of Cell Biology* 122(2): 283–293 (1993).

Wiedmann, et al., "Ligase Chain Reaction (LCR)—Overview and Applications," *PCR Methods and Applications* (Cold Spring Harbor Laboratory Press, Cold Spring Harbor Laboratory, NY, 1994) pp. S51–S64.

Winn–Deen, et al., "Non–radioactive detection of *Mycobacterium tuberculosis* LCR products in a microtitre plate format," *Molecular and Cellular Probes* (England) 7(3):179–186 (1993).

Young & Anderson, "Quantitative analysis of solution hybridisation," *Nucleic Acid Hybridisation: A Practical Approach* pp. 47–71 (IRL Press, 1985).

Yu, et al., "Cyanine dye dUTP analogs for enzymatic labeling of DNA probes," *Nucleic Acids Research* 22(15): 3226–3232 (1994).

Zehavi, et al., "Light sensitive glycosides. I. 6–Nitoveratryl β–D–Glucopyranoside and 2–Nitrobenzyl β–D–Glucopyranoside," *J. Organic Chem*. 37:2281–2288 (1972).

Zhu & Ito, "Purification and characterization of PRD1 DNA polymerase," *Biochimica Biophysica Acta* 1219(2): 267–276 (1994).

Zijderveld & Van Der Vliet, "Helix–Destabilizing Properties of the Adenovirus DNA–Binding Protein," *Journal of Virology* 68(2):1158–1164 (1994).

Unrau & Deugau, "Non–cloning amplification of specific DNA fragments from whole genomic DNA digests using DNA 'indexers'" *Gene* 145:163–9 (1994).

White, et al., "Concatemer chain reaction: A Taq DNA polymerase–mediated mechanism for generating long tandemly repetitive DNA sequences," *Analytical Biochemistry* 199:184–90 (1991).

Zhang, et al., "Amplification of target–specific, ligation–dependent circular probe," *Gene* 211:277–85 (1998).

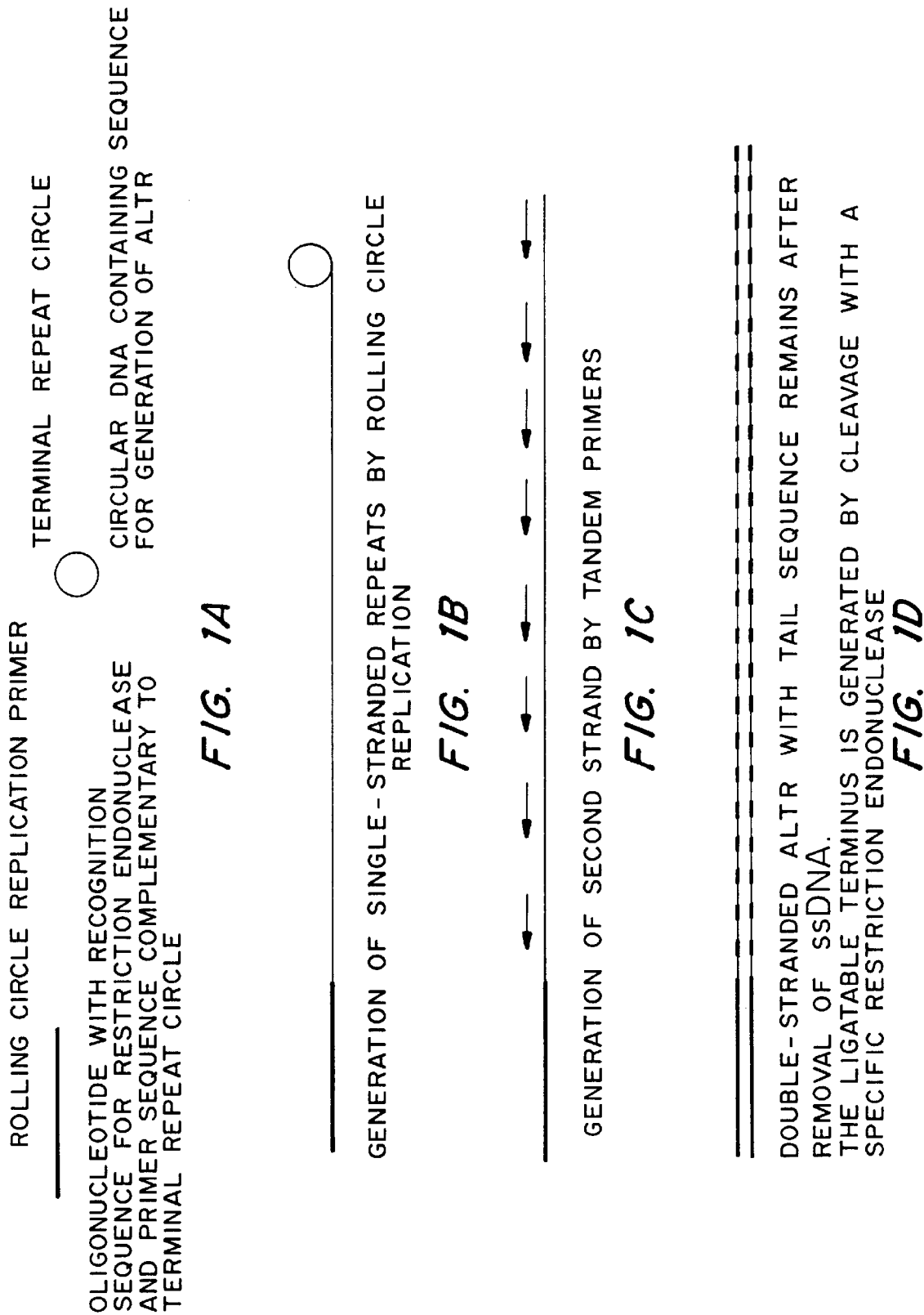

GENOMIC DNA FRAGMENT

*FIG. 2A*

ALTR

LIGATION REACTION

*FIG. 2B*

ALTR

GENOMIC DNA FRAGMENT WITH LIGATED ALTRs

*FIG. 2C*

SEQUENCE LISTING

```
<160> NUMBER OF SEQ ID NOS: 9

<210> SEQ ID NO: 1
<211> LENGTH: 64
<212> TYPE: DNA
<213> ORGANISM: Artificial Sequence
<220> FEATURE:
<223> OTHER INFORMATION: Description of Artificial Sequence: ALTR with
      identical repeats and identical linkers
<221> NAME/KEY: misc_feature
<222> LOCATION: (25)..(27)
<223> OTHER INFORMATION: Linker sequence where N represents A, G, C, or
      T
<221> NAME/KEY: misc_feature
<222> LOCATION: (28)..(37)
<223> OTHER INFORMATION: DNA insert where N represents A, G, C, or T
<221> NAME/KEY: misc_feature
<222> LOCATION: (38)..(40)
<223> OTHER INFORMATION: Linker Sequence where N represents A, G, C, or
      T

<400> SEQUENCE: 1
aggtaggtag gtaggtaggt aggtnnnnnn nnnnnnnnnn acctacctac ctacctacct    60
acct                                                                64
```

```
<210> SEQ ID NO: 2
<211> LENGTH: 64
<212> TYPE: DNA
<213> ORGANISM: Artificial Sequence
<220> FEATURE:
<223> OTHER INFORMATION: Description of Artificial Sequence: ALTR with
      identical repeats and different linkers
<221> NAME/KEY: misc_feature
<222> LOCATION: (25)..(27)
<223> OTHER INFORMATION: Linker Sequence where N represents A, G, C, or
      T
<221> NAME/KEY: misc_feature
<222> LOCATION: (28)..(37)
<223> OTHER INFORMATION: DNA insert where N represents A, G, C, or T
<221> NAME/KEY: misc_feature
<222> LOCATION: (38)..(40)
<223> OTHER INFORMATION: Linker Sequence where N represents A, G, C, or
      T

<400> SEQUENCE: 2
aggtaggtag gtaggtaggt aggtnnnnnn nnnnnnnnnn acctacctac ctacctacct      60
acct                                                                  64

<210> SEQ ID NO: 3
<211> LENGTH: 64
<212> TYPE: DNA
<213> ORGANISM: Artificial Sequence
<220> FEATURE:
<223> OTHER INFORMATION: Description of Artificial Sequence: ALTR with
      two types of ALTR repeats and different linkers
<221> NAME/KEY: misc_feature
<222> LOCATION: (25)..(27)
<223> OTHER INFORMATION: Linker Sequence where N represents A, G, C, or
      T
<221> NAME/KEY: misc_feature
<222> LOCATION: (28)..(37)
<223> OTHER INFORMATION: DNA insert where N represents A, G, C, or T
<221> NAME/KEY: misc_feature
<222> LOCATION: (38)..(40)
<223> OTHER INFORMATION: Linker Sequence where N represents A, G, C, or
      T

<400> SEQUENCE: 3
aggtaggtag gtaggtaggt aggtnnnnnn nnnnnnnnnn gatggatgga tggatggatg      60
gatg                                                                  64

<210> SEQ ID NO: 4
<211> LENGTH: 34
<212> TYPE: DNA
<213> ORGANISM: Artificial Sequence
<220> FEATURE:
<223> OTHER INFORMATION: Description of Artificial Sequence: Repeat A

<400> SEQUENCE: 4
acgcagctcg tgtaatacga ctcgcatgcc tccc                                 34

<210> SEQ ID NO: 5
<211> LENGTH: 22
<212> TYPE: DNA
<213> ORGANISM: Artificial Sequence
<220> FEATURE:
<223> OTHER INFORMATION: Description of Artificial Sequence: Primer A

<400> SEQUENCE: 5
cgcagctcgt gtaatacgac tc                                              22

<210> SEQ ID NO: 6
```

```
<211> LENGTH: 34
<212> TYPE: DNA
<213> ORGANISM: Artificial Sequence
<220> FEATURE:
<223> OTHER INFORMATION: Description of Artificial Sequence: Repeat B

<400> SEQUENCE: 6
atgcatgctc agtggtgctg agtaacagcc tggg                                34

<210> SEQ ID NO: 7
<211> LENGTH: 22
<212> TYPE: DNA
<213> ORGANISM: Artificial Sequence
<220> FEATURE:
<223> OTHER INFORMATION: Description of Artificial Sequence: Primer B

<400> SEQUENCE: 7
ggctgttact cagcaccact ga                                             22

<210> SEQ ID NO: 8
<211> LENGTH: 75
<212> TYPE: DNA
<213> ORGANISM: Artificial Sequence
<220> FEATURE:
<223> OTHER INFORMATION: Description of Artificial Sequence: Left side
      of ALTR vector
<221> NAME/KEY: misc_feature
<222> LOCATION: (69)..(75)
<223> OTHER INFORMATION: Insert and polylinker sequences where N
      represents A, G, C, or T

<400> SEQUENCE: 8
acgcagctcg tgtaatacga ctcgcatgcc tcccacgcag ctcgtgtaat acgactcgca    60
tgcctcccnn nnnnn                                                     75

<210> SEQ ID NO: 9
<211> LENGTH: 75
<212> TYPE: DNA
<213> ORGANISM: Artificial Sequence
<220> FEATURE:
<223> OTHER INFORMATION: Description of Artificial Sequence: Right side
      of ALTR vector
<221> NAME/KEY: misc_feature
<222> LOCATION: (1)..(7)
<223> OTHER INFORMATION: Insert and Polylinker Sequences where N
      represents A, G, C, or T

<400> SEQUENCE: 9
nnnnnnnggg atgcatgctc agtggtgctg agtaacagcc tgggatgcat gctcagtggt    60
gctgagtaac agcct                                                     75
```

ARTIFICIAL LONG TERMINAL REPEAT VECTORS

CROSS-REFERENCE TO RELATED APPLICATIONS

This application claims benefit of U.S. Provisional Application No. 60/100,305, filed Sep. 15, 1999. application Ser. No. 60/100,305, filed Sep. 15, 1998, is hereby incorporated herein by reference.

BACKGROUND OF THE INVENTION

The disclosed invention is generally in the field of nucleic acid amplification.

DNA molecular cloning is routinely carried out using plasmid, phage, or viral vectors that replicate inside cells. Genomic cloning is routinely carried out using vectors that replicate inside cells. While existing cloning methods work quite well for most genomic fragments, certain DNA domains tend to suffer alterations, notably deletions or rearrangements. A method, in which individual DNA molecules are cloned in solution by serial dilution and subsequent PCR amplification from tubes containing single molecules has been described (Lukyanov et al., *Nucleic Acid Research* 24:2194–2195 (1996)). A method has also been described for cloning RNA populations derived from single RNA molecules in an immobilized medium (Chetverina and Chetverin, *Nucleic Acids Research* 21:2349–2353 (1993)). While both of these methods allow in vitro cloning, neither is practical for cloning of large fragments.

A number of methods have been developed for exponential amplification of nucleic acids. These include the polymerase chain reaction (PCR), ligase chain reaction (LCR), self-sustained sequence replication (3SR), nucleic acid sequence based amplification (NASBA), strand displacement amplification (SDA), and amplification with Qβ replicase (Birkenmeyer and Mushahwar, *J. Virological Methods*, 35:117–126 (1991); Landegren, *Trends Genetics* 9:199–202 (1993)).

Current methods of PCR amplification involve the use of two primers which hybridize to the regions flanking a nucleic acid sequence of interest such that DNA replication initiated at the primers will replicate the nucleic acid sequence of interest. By separating the replicated strands from the template strand with a denaturation step, another round of replication using the same primers can lead to geometric amplification of the nucleic acid sequence of interest. PCR amplification has the disadvantage that the amplification reaction cannot proceed continuously and must be carried out by subjecting the nucleic acid sample to multiple cycles in a series of reaction conditions. PCR also has the disadvantage that the length of nucleic acid that can be effectively amplified is limited.

Accordingly, there is a need for a cloning and amplification method that allows amplification of longer nucleic acid segments and that is less complicated, are more reliable, and produces greater amplification in a shorter time.

It is therefore an object of the disclosed invention to provide an in vitro method of cloning and amplifying a target nucleic acid sequence in a continuous, isothermal reaction.

It is another object of the disclosed invention to provide an in vitro method of cloning and amplifying a target nucleic acid sequence where multiple copies of the target nucleic acid sequence are produced in a single amplification cycle.

It is another object of the disclosed invention to provide a kit for cloning and amplifying a target nucleic acid sequence in a continuous, isothermal reaction.

BRIEF SUMMARY OF THE INVENTION

Disclosed are compositions and an in vitro method for cloning and/or amplification of nucleic acid sequences of interest. The method is based on strand displacement replication of the nucleic acid sequences by multiple priming on artificial long terminal repeat (ALTR) sequences appended to the ends of the nucleic acid molecule of interest. The target sequences for cloning and amplification can be very long, up to 40 to 80 Kb or longer. In a preferred form of the method, a single primer is used to prime strand displacement replication at multiple sites in artificial long terminal repeat sequences, flanking a target nucleic acid, containing multiple tandem repeats of a primer complement sequence. Amplification proceeds by replication initiated at each primer and continuing through the target nucleic acid sequence.

A key feature of this method is the displacement of intervening primers during replication. Once the nucleic acid strands elongated from the right ALTR reaches the left ALTR, and vice versa, another round of priming and replication will take place. This allows multiple copies of a nested set of the target nucleic acid sequence to be synthesized in a short period of time. This nested replication of multiple copies significantly increases the amplification yield for extremely long target sequences since copies of the target sequence are produced simultaneously, not sequentially as in PCR. By using a sufficient number of repeat units in the ALTRs, and thus a sufficient number of primer complement sequences, only a few rounds of replication are required to produce hundreds of thousands of copies of the nucleic acid sequence of interest.

The disclosed method has advantages over the polymerase chain reaction since it can be carried out under isothermal conditions. No thermal cycling is needed because the polymerase at the head of an elongating strand (or a compatible strand-displacement protein) will displace, and thereby make available for hybridization, the strand ahead of it. Other advantages of the disclosed method include the ability to amplify very long nucleic acid segments (on the order of 80 kilobases) and rapid amplification of shorter segments (10 kilobases or less). In the disclosed method, single priming events at unintended sites will not lead to artifactual amplification at these sites (since amplification at the intended site will quickly outstrip the single strand replication at the unintended site).

A preferred form of the disclosed method makes use of indexed artificial long terminal repeats that allow amplification and identification of specific nucleic acid fragments present in a mixture of nucleic acid fragments without requiring any knowledge of the sequence of the nucleic acid fragment. This is accomplished by digesting a nucleic acid sample, such a genomic DNA, with a restriction enzyme having an interrupted palindrome recognition sequence or a cleavage site offset from the recognition site (interrupted palindrome and class-IIS restriction enzymes). The resulting fragments having a random distribution of sticky ends are then ligated to pairs of indexed ALTRs in separate reactions collectively representing every combination of indexed ALTRs. The indexed ALTRs each have a different sticky end and the set of ALTRs collectively include all of the possible sticky ends that can be generated by the restriction enzyme used. Thus, in each ligation reaction, only those nucleic acid fragments having sticky ends complementary to the sticky ends of the specific pair of ALTRs present in the reaction will have an ALTR added to each end. As a result, only these fragments to which ALTRs have been added will be amplified. Alternatively, all of the ALTRs can be used together in the same reaction to clone and amplify all of the compatible fragments in a nucleic acid sample. In the resulting mixture of clones, a clone of interest, if identified, can be separately amplified by identifying the ALTRs flanking the clone and using the same ALTRs to clone the fragment individually. Once identified, the same nucleic acid fragment can be cloned from the same source using the same pair of ALTRs that resulting in the original amplification.

Following amplification, the amplified sequences can be for any purpose, such as uses known and established for PCR amplified sequences. For example, amplified sequences can be detected using any of the conventional detection systems for nucleic acids such as detection of fluorescent labels, enzyme-linked detection systems, antibody-mediated label detection, and detection of radioactive labels. The amplified sequences can also be used to long nucleic acids for pharmaceutical uses, such as for multi-antigen vaccines, that are free of contaminating proteins and other cellular components that are present in nucleic acid replicated in cells.

A key feature of the disclosed method is that amplification takes place not in cycles, but in a continuous, isothermal replication. This makes amplification less complicated and much more consistent in output. Strand displacement allows rapid generation of multiple copies of a nucleic acid sequence or sample in a single, continuous, isothermal reaction. DNA that has been produced using the disclosed method can then be used for any purpose or in any other method desired. For example, PCR can be used to further amplify any specific DNA sequence that has been previously amplified by the disclosed method.

BRIEF DESCRIPTION OF THE DRAWINGS

FIGS. 1A, 1B, 1C, and 1D are diagrams of steps in the formation of an artificial long terminal repeat using rolling circle replication of a terminal repeat circle.

FIG. 2 is a diagram illustrating formation of an artificial long terminal repeat vector.

DETAILED DESCRIPTION OF THE INVENTION

Figure 4:
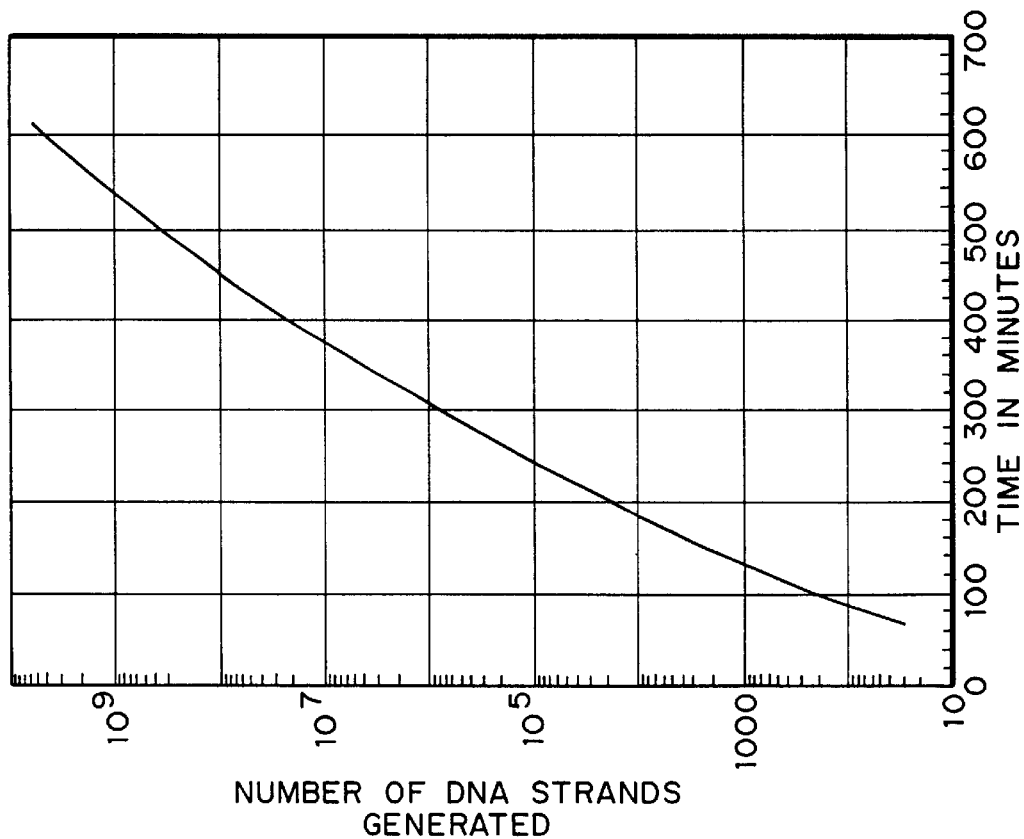
FIG. 4 is a graph of the number of DNA strands generated in the disclosed method versus time when amplifying a 65 kb insert using 48 repeat ALTRs.

Disclosed are compositions and an in vitro method for cloning and amplification of nucleic acid sequences of interest. The method is based on strand displacement replication of the nucleic acid sequences by multiple priming on artificial long terminal repeat (ALTR) sequences appended to the ends of the nucleic acid molecule of interest. The target sequences for cloning and amplification can be very long, up to 40 to 80 Kb or longer. In a preferred form of the method, a single primer is used to prime strand displacement replication at multiple sites in artificial long terminal repeat sequences, flanking a target nucleic acid, containing multiple tandem repeats of a primer complement sequence. Amplification proceeds by replication initiated at each primer and continuing through the target nucleic acid sequence.

A key feature of this method is the displacement of intervening primers during replication. Once the nucleic acid strands elongated from the right ALTR reaches the left ALTR, and vice versa, another round of priming and replication will take place. This allows multiple copies of a nested set of the nucleic acid molecule to be synthesized in a short period of time. This nested replication of multiple copies significantly increases the amplification yield for extremely long target sequences since copies of the target sequence are produced simultaneously, not sequentially as in PCR. By using a sufficient number of repeat units in the ALTRs, and thus a sufficient number of primer complement sequences, only a few rounds of replication are required to produce hundreds of thousands of copies of the nucleic acid sequence of interest.

The disclosed method has advantages over the polymerase chain reaction since it can be carried out under isothermal conditions. No thermal cycling is needed because the polymerase at the head of an elongating strand (or a compatible strand-displacement protein) will displace, and thereby make available for hybridization, the strand ahead of it. Other advantages of the disclosed method include the ability to amplify very long nucleic acid segments (on the order of 80 kilobases) and rapid amplification of shorter segments (10 kilobases or less). In the disclosed method, single priming events at unintended sites will not lead to artifactual amplification at these sites (since amplification at the intended site will quickly outstrip the single strand replication at the unintended site).

A preferred form of the disclosed method makes use of indexed artificial long terminal repeats that allow amplification and identification of specific nucleic acid fragments present in a mixture of nucleic acid fragments without requiring any knowledge of the sequence of the nucleic acid fragment. This is accomplished by digesting a nucleic acid sample, such a genomic DNA, with a restriction enzyme having an interrupted palindrome recognition sequence or a cleavage site offset from the recognition site (interrupted palindrome and class-IIS restriction enzymes). The resulting fragments having a random distribution of sticky ends are then ligated to pairs of indexed ALTRs in separate reactions collectively representing every combination of indexed ALTRs. The indexed ALTRs each have a different sticky end and the set of ALTRs collectively include all of the possible sticky ends that can be generated by the restriction enzyme used. Thus, in each ligation reaction, only those nucleic acid fragments having sticky ends complementary to the sticky ends of the specific pair of ALTRs present in the reaction will have an ALTR added to each end. As a result, only these fragments to which ALTRs have been added will be amplified. Alternatively, all of the ALTRs can be used together in the same reaction to clone and amplify all of the compatible fragments in a nucleic acid sample. In the resulting mixture of clones, a clone of interest, if identified, can be separately amplified by identifying the ALTRs flanking the clone and using the same ALTRs to clone the fragment individually. Once identified, the same nucleic acid fragment can be cloned from the same source using the same pair of ALTRs that resulting in the original amplification.

Following amplification, the amplified sequences can be for any purpose, such as uses known and established for PCR amplified sequences. For example, amplified sequences can be detected using any of the conventional detection systems for nucleic acids such as detection of fluorescent labels, enzyme-linked detection systems, antibody-mediated label detection, and detection of radioactive labels. The amplified sequences can also be used to long nucleic acids for pharmaceutical uses, such as for multi-antigen vaccines, that are free of contaminating proteins and other cellular components that are present in nucleic acid replicated in cells.

A key feature of the disclosed method is that amplification takes place not in cycles, but in a continuous, isothermal replication. This makes amplification less complicated and much more consistent in output. Strand displacement allows rapid generation of multiple copies of a nucleic acid sequence or sample in a single, continuous, isothermal reaction. DNA that has been produced using the disclosed method can then be used for any purpose or in any other method desired. For example, PCR can be used to further amplify any specific DNA sequence that has been previously amplified by the disclosed method.

In Nature, certain DNA sequences are known contain direct repeats. Other sequences are known to contain inverted repeats. This disclosed method uses an unnatural object, the Artificial Long Terminal Repeat vector, which contains either the same type of repeats at both ends, or preferably, two different kinds of repeats on either end. The resulting molecule comprises one array of identical repeats on one side, and another array of identical repeats on the other side of a DNA insert (DDDDD). The repeats are joined by linker sequences (LLL or SSS), which may be identical for any given construct (as in example ALTR 1, below), or different for any given construct (as in example ALTRs 2 and 3, below).

Example ALTR vector configurations are illustrated diagrammatically below. In these examples four base repeats were used to save space. The preferred repeat length is much longer, as discussed elsewhere herein. For all of these configurations, the replication of each DNA strand occurs through the binding and extension of a single DNA primer at multiple sites in the ALTR sequence.

1. ALTR with identical repeats and identical linkers (SEQ ID NO:1)

```
AGGT>AGGT>AGGT>AGGT>AGGT>AGGT>LLL>DDDDDDDDDD
TCCA<TCCA<TCCA<TCCA<TCCA<TCCA<LLL>DDDDDDDDDD

>LLL>ACCT>ACCT>ACCT>ACCT>ACCT>ACCT
                <LLL<TGGA<TGGA<TGGA<TGGA<TGGA<TGGA
```

2. ALTR with identical repeats and different linkers (SEQ ID NO:2)

```
AGGT>AGGT>AGGT>AGGT>AGGT>AGGT>LLL>DDDDDDDDDD
TCCA<TCCA<TCCA<TCCA<TCCA<TCCA<LLL>DDDDDDDDDD

>SSS>ACCT>ACCT>ACCT>ACCT>ACCT>ACCT
                <SSS<TGGA<TGGA<TGGA<TGGA<TGGA<TGGA
```

3. ALTR with two types of ALTR repeats and different linkers (SEQ ID NO:3)

```
AGGT>AGGT>AGGT>AGGT>AGGT>AGGT>LLL>DDDDDDDDDD
TCCA<TCCA<TCCA<TCCA<TCCA<TCCA<LLL>DDDDDDDDDD

>SSS>GATG>GATG>GATG>GATG>GATG>GATG
                <SSS<CTAC<CTAC<CTAC<CTAC<CTAC<CTAC
```

The disclosed method has several advantageous features. A few are listed below.

a) Can be generated by isothermal amplification starting from a few molecules b) Can generate clonal DNA populations in a test tube c) No selection against coding sequences that may be deleterious to *E. coli* d) Can be made to incorporate of modified bases as dNTPs e) Can be made with chemically modified 5'-termini by simply using suitably modified primers in the amplification reaction.

f) Simple purification after in vitro synthesis g) Increased purity (freedom from bacterial cell contaminants such as pyrogens).

The disclosed method, and the nucleic acid molecules amplified in the disclosed method can be used for a number of purposes. For example:

1. Gene mapping analysis of genomic DNA or long cDNAs.
2. Analysis of chromosomal translocations.
3. Automated manipulation and sequencing of genomic DNA or long cDNAs.
4. Sequencing of genomic DNA
5. Exon trapping of genomic DNA There are a number of other applications which require the use of large DNA molecules. Examples of such applications occur in the field of DNA vaccines. DNA vaccine vectors may contain a number of coding sequences, designed to produce a multiplicity of antigens. As knowledge of vaccine antigens improves, there is a growing tendency to create vectors that combine many antigen-coding genes in a concatenated arrangement. Currently, bacterial plasmids are used as vectors for DNA vaccine construction.

One embodiment of the disclosed method is a method of amplifying a target nucleic acid sequence, where the method involves (a) replicating a terminal repeat circle by rolling circle replication primed by a rolling circle replication primer to form an artificial long terminal repeat, (b) ligating the artificial long terminal repeat to the ends of a target nucleic acid sequence to form an artificial long terminal repeat vector, (c) amplifying the artificial long terminal repeat vector by strand displacement replication primed by one or more strand displacement primers, where the target nucleic acid sequence is amplified.

Another embodiment of the disclosed method is a method of amplifying a target nucleic acid sequence, where the method involves (a) ligating artificial long terminal repeats to the ends of a target nucleic acid sequence to form an artificial long terminal repeat vector, (b) amplifying the artificial long terminal repeat vector by strand displacement replication primed by one or more strand displacement primers, where the target nucleic acid sequence is amplified.

Another embodiment of the disclosed method is a method of amplifying a target nucleic acid sequence, where the method involves (a) ligation of multiple identical repeat units to form an artificial long terminal repeat, (b) ligating the artificial long terminal repeat to the ends of a target nucleic acid sequence to form an artificial long terminal repeat vector, (c) amplifying the artificial long terminal repeat vector by strand displacement replication primed by one or more strand displacement primers, where the target nucleic acid sequence is amplified.

Another embodiment of the disclosed method is a method of amplifying nucleic acid molecules, where the method involves (a) digesting a nucleic acid sample with a type II restriction endonuclease having an interrupted palindrome recognition sequence or a type IIS restriction enzyme to produce nucleic acid molecules with cohesive ends, (b) ligating artificial long terminal repeats to the ends of the nucleic acid molecules to form artificial long terminal repeat vectors, (c) amplifying the artificial long terminal repeat vectors by strand displacement replication primed by one or more strand displacement primers, where the nucleic acid molecule is amplified.

The method can be practiced and expanded in several ways. For example, the amplification of the artificial long terminal repeat vector can be primed by a single strand displacement primer. The amplification can be performed under substantially isothermic conditions. The amplification can be performed without thermal cycling. The artificial long terminal repeats can each have at least five repeat units. The artificial long terminal repeats can each have at least 25 repeat units. The artificial long terminal repeat can be produced by replicating a terminal repeat circle by rolling circle replication primed by a rolling circle replication primer. The artificial long terminal repeat can be made double-stranded by performing the rolling circle replication in the presence of helicase, primase, ligase, and single-stranded DNA binding protein. The artificial long terminal repeat can be made double-stranded by ligating together oligonucleotides hybridized to the artificial long terminal repeat strand made during the rolling circle replication.

The disclosed method can also use a set of artificial long terminal repeats in step (b), where each member of the set has a different cohesive end, and where the cohesive ends of the members of the set collectively include complements to all possible cohesive ends that can be generated by cleavage with the restriction endonuclease, such that the artificial long terminal repeat ligated on each end of the nucleic acid molecules depends on the sequences of the cohesive ends of each nucleic acid molecule. In such an embodiment, step (b) can be performed as multiple separate reactions where each reaction has a different pair of artificial long terminal repeats.

Also disclosed is a kit for amplifying a target nucleic acid sequence, the kit including an artificial long terminal repeat, where the artificial long terminal repeat comprises tandem repeat units and a tail sequence at one end, and a strand displacement primer, where the strand displacement primer is complementary to a sequence in, or straddling, the repeat units. The kit can also include a strand displacing DNA polymerase or a DNA polymerase and a compatible strand displacement factor. Also disclosed is a kit for amplifying a target nucleic acid sequence, the kit including a repeat circle, where the repeat circle is a single-stranded circular DNA molecule, a rolling circle replication primer including a sequence complementary to a sequence in the repeat circle, and a tail sequence, and a strand displacement primer, where the strand displacement primer is complementary to a sequence in, or straddling, the repeat units.

I. Materials

A. Nucleic Acid Molecules

Nucleic acid molecules for cloning and amplification in the disclosed method can be any nucleic acid. A nucleic acid molecule for use in the disclosed method can be in any nucleic acid sample of interest. The source, identity, and preparation of many such nucleic acid samples are known. The nucleic acid molecules can come from any source such as a cellular or tissue nucleic acid sample, a subclone of a previously cloned fragment, mRNA, chemically synthesized nucleic acid, genomic nucleic acid samples, nucleic acid molecules obtained from nucleic acid libraries, specific nucleic acid molecules, and mixtures of nucleic acid molecules. Since the disclosed method is particularly suited to amplification of very large molecules (up to 80 Kb or larger), genomic nucleic acid samples are particular preferred as a source for nucleic acid molecules. The nucleic acid sample can be a nucleic acid sample from a single cell. Preferred nucleic acid molecules are those which are difficult to amplify using PCR due to, for example, length or composition.

In the method, the nucleic acid molecule is flanked by artificial long terminal repeats (ALTRs). Preferably this is accomplished by ligation of the ALTRs to the nucleic acid molecule, although any suitable coupling mechanism can also be used. Thus, the only requirement for nucleic acids molecules to be used in the disclosed method is that they can be coupled to the end of an ALTR. Single-stranded nucleic acid molecules, such as RNA, can be used by converting the molecule to be double-stranded. In the case of RNA molecules, this can be accomplished, for example, by producing a cDNA molecule of the RNA. Numerous methods are known for preparing and inserting nucleic acid molecules into vectors and any of these can be used to prepare nucleic acid molecules for use in the disclosed method (see, for example, Sambrook et al., *Molecular Cloning: A Laboratory Manual*, 2nd Edition (Cold Spring Harbor Laboratory Press, Cold Spring Harbor, N. Y., 1989)).

Preferably, the nucleic acid molecule is prepared by generating cohesive ends (sticky ends) to facilitate attachment of ALTRs. This can be accomplished, for example by cleaving a nucleic acid molecule of interest, or a nucleic acid sample, with a restriction enzyme, or by adding linkers to the ends of nucleic acid molecules of interest that have, or can be processed to have sticky ends. One or both of the ends of the nucleic acid molecule can also be left blunt ended, although this is not preferred. The two ends of nucleic acid molecules to be used in the disclosed method can also be made different to allow directional ligation of different ALTRs. For example, the to ends can have different sticky ends, or have one sticky end and one blunt end.

For cloning with indexed artificial long terminal repeats, the nucleic acid molecules should be prepared by cleavage with a restriction enzyme having an interrupted palindrome or a cleavage site that is offset from the recognition sequence. Preferred restriction enzymes having an interrupted palindrome are type II restriction enzymes having degeneracy in the recognition/cleavage sequence around the site of cleavage. Preferred restriction enzymes having a cleavage site that is offset from the recognition sequence are type IIS restriction enzymes. These restriction enzymes will produce nucleic acid molecules having a distribution of sequences represented in their cohesive ends. This allows ligation of different indexed ALTRs depending on the actual sequence of the cohesive ends present on a given nucleic acid molecule.

B. Rolling Circle Replication Primers

Rolling circle replication primers are used with the disclosed method to produce artificial long terminal repeats by priming rolling circle replication of terminal repeat circles. A rolling circle replication primer (RCRP) is an oligonucleotide having sequence complementary to the primer complement portion of a terminal repeat circle. This sequence is referred to as the complementary portion of the RCRP. The complementary portion of a RCRP and the cognate primer complement portion can have any desired sequence so long as they are complementary to each other. In general, the sequence of the RCRP can be chosen such that it is not significantly complementary to any other portion of the terminal repeat circle. The complementary portion of a rolling circle replication primer can be any length that supports specific and stable hybridization between the primer and the primer complement portion. Generally this is 10 to 35 nucleotides long, but is preferably 16 to 20 nucleotides long.

It is preferred that rolling circle replication primers also contain additional sequence at the 5' end of the RCRP that is not complementary to any part of the terminal repeat circle. This sequence is referred to as the tail sequence of the RCRP. The tail sequence preferably contains one or more restriction sites for cleavage by restriction enzymes. These sites serve to facilitate ligation of artificial long terminal repeats to nucleic acid molecules. This purpose is aided by the location of the tail sequence at the end of ALTR sequence produced by rolling circle replication primed by the rolling circle replication primer.

The tail sequence of the RCRP also serves to facilitate strand displacement during DNA replication. The tail sequence of a RCRP may be any length, but is generally 1 to 200 nucleotides long, and preferably 30 to 100 nucleotides long. The rolling circle replication primer may also include modified nucleotides to make it resistant to exonuclease digestion. For example, the primer can have three or four phosphorothioate linkages between nucleotides at the 5' end of the primer.

C. Strand Displacement Primers

Strand displacement primers for use in the disclosed amplification method are oligonucleotides having sequence complementary to sequence in, or straddling, the repeat unit of the artificial long terminal repeat. This sequence is referred to as the complementary portion of the strand displacement primer. This relationship ensures that there are multiple primer complement sequences in the ALTR (one for every repeat unit in the ALTR). The complementary portion of a strand displacement primer can be any length that supports specific and stable hybridization between the strand displacement primer and the ALTR. Generally this is 10 to 35 nucleotides long, but is preferably 16 to 24 nucleotides long.

It is preferred that strand displacement primers also contain additional sequence at the 5' end of the strand displacement primer that is not complementary to the ALTR. This sequence is referred to as the non-complementary portion of the strand displacement primer. The non-complementary portion of the strand displacement primer, if present, serves to facilitate strand displacement during DNA replication. The non-complementary portion of the strand displacement primer can also include a functional sequence such as a promoter for an RNA polymerase. The non-complementary portion of a strand displacement primer may be any length, but is generally 1 to 100 nucleotides long, and preferably 4 to 8 nucleotides long.

It is preferred that, when hybridized to an ALTR, the strand displacement primers are separated from each other. The amount of separation between adjacent, hybridized strand displacement primers is a function of the length of the repeat unit and the length of the complementary portion of the primer. The longer the repeat unit, the greater the separation. The longer the complementary portion of the primer, the shorter the separation. It is preferred that, when hybridized, the strand displacement primers are separated from each other by at least 5 bases. It is more preferred that, when hybridized, the strand displacement primers are separated from each other by at least 10 bases. It is still more preferred that, when hybridized, the strand displacement primers are separated from each other by at least 20 bases. It is still more preferred that, when hybridized, the strand displacement primers are separated from each other by at least 30 bases. It is still more preferred that, when hybridized, the strand displacement primers are separated from each other by at least 40 bases. It is still more preferred that, when hybridized, the strand displacement primers are separated from each other by at least 50 bases.

It is preferred that, when hybridized, the strand displacement primers are separated from each other by no more than about 500 bases. It is more preferred that, when hybridized, the strand displacement primers are separated from each other by no more than about 400 bases. It is still more preferred that, when hybridized, the strand displacement primers are separated from each other by no more than about 300 bases. It is still more preferred that, when hybridized, the strand displacement primers are separated from each other by no more than about 200 bases. Any combination of the preferred upper and lower limits of separation described above are specifically contemplated, including all intermediate ranges. There need not be any separation between strand displacement primers.

The optimal separation distance between strand displacement primers will not be the same for all DNA polymerases, because this parameter is dependent on the net polymerization rate. A processive DNA polymerase will have a characteristic polymerization rate which may range from 5 to 300 nucleotides per second, and may be influenced by the presence or absence of accessory ssDNA binding proteins and helicases. In the case of a non-processive polymerase, the net polymerization rate will depend on the enzyme concentration, because at higher concentrations there are more re-initiation events and thus the net polymerization rate will be increased. An example of a processive polymerase is φ29 DNA polymerase, which proceeds at 50 nucleotides per second. An example of a non-processive polymerase is Vent exo(–) DNA polymerase, which will give effective polymerization rates of 4 nucleotides per second at low concentration, or 16 nucleotides per second at higher concentrations.

To obtain an optimal yield in a strand displacement replication reaction, the primer spacing is preferably adjusted to suit the polymerase being used. Long primer spacing is preferred when using a polymerase with a rapid polymerization rate. Shorter primer spacing is preferred when using a polymerase with a slower polymerization rate. The following assay can be used to determine optimal spacing with any polymerase. The artificial long terminal repeats are designed for the same strand displacement primer, but with different repeat unit lengths. The repeat unit length is varied systematically between in increments of 25 nucleotides within the range of 10 nucleotides to 410 nucleotides. A series of reactions are performed in which the different ALTR vectors are amplified using the same strand displacement primer. The spacing that produces the highest experimental yield of DNA is the optimal primer spacing for the specific DNA polymerase, or DNA polymerase plus accessory protein combination being used.

DNA replication initiated at the sites in the ALTR vector where the primers hybridize will extend to and displace strands being replicated from primers hybridized at adjacent sites. Displacement of an adjacent strand makes it available for hybridization to another primer and subsequent initiation of another round of replication.

Where indexed ALTRs are used, the strand displacement primer is preferably a single universal primer that can prime all of the ALTRs. For specific amplification in a mixture of ALTR vectors using a mixture of indexed ALTRs, a strand displacement primer specific for a specific ALTR may be used. Such a strand displacement prier is referred to as an indexed strand displacement primer. This can be accomplished by including both common sequences (common to all of the indexed ALTRs) and individual sequences (each present only in one of the indexed ALTRs) in the repeat units of the indexed ALTRs. The complementary portions of the indexed strand displacement primers are complementary to an individual sequence in one (or a subset) of the indexed ALTRs.

Since indexed ALTRs are used in pairs, the strand displacement primers may consist of a universal pair of primers, one designed to bind the first ALTR and the other designed to bind the second ALTR of each indexing pair. In such embodiments, there is one universal primer specific for the first strand, and one (different) universal primer specific for the second strand. This universal set of two primers may be used for all pairs of ALTRs.

D. Terminal Repeat Circles

An terminal repeat circle (TRC) is a circular single-stranded DNA molecule, generally containing between 40 to 1000 nucleotides, preferably between about 50 to 150 nucleotides, and most preferably between about 50 to 100 nucleotides. Portions of TRCs have specific functions making the TRC useful for production of artificial long terminal repeats (ALTRs). Generally, an terminal repeat circle is a single-stranded, circular DNA molecule comprising a primer complement portion and a primer portion. The primer complement portion is complementary to the complementary portion of a rolling circle replication primer. The primer portion matches the complementary portion of a strand displacement primer. This arrangement allows strand displacement primers to prime synthesis from the ALTRs into the nucleic acid molecule flanked by the ALTRs.

Those segments of the TRC that do not correspond to a specific portion of the TRC can be arbitrarily chosen sequences. It is preferred that TRCs do not have any sequences that are self-complementary. It is considered that this condition is met if there are no complementary regions greater than six nucleotides long without a mismatch or gap. It is also preferred that TRCs containing a promoter portion do not have any sequences that resemble a transcription terminator, such as a run of eight or more thymidine nucleotides.

A terminal repeat circle, when replicated, gives rise to a long DNA molecule containing multiple repeats of sequences complementary to the terminal repeat circle. This long DNA molecule is referred to herein as an artificial long terminal repeat (ALTR). An ALTR contains sequences complementary to the primer complement portions. These sequences in the ALTR are referred to as rolling circle primer sequences (which match the sequence of the rolling circle replication primer) and strand displacement primer complement sequences (which are complementary to the strand displacement primer).

Where indexed ALTRs are used, there is a terminal repeat circle for each indexed ALTR. Each indexed TRC can include both a common primer portion (common to all TRCs) and an indexed primer portion having an individual sequence for each indexed TRC. This allows strand displacement replication of all indexed ALTR vectors with a universal strand displacement primer, or strand displacement replication of individual indexed ALTR vectors using a strand displacement primer specific for the specific indexed ALTR.

E. Artificial Long Terminal Repeats

Artificial long terminal repeats (ALTRs) are long nucleic acid molecules with tandemly repeated sequences. Each instance of the repeated sequence is referred to as a repeat unit. ALTRs have a tail sequence at one end to facilitate attachment of the ALTR to a nucleic acid molecule of interest. ALTRs are used in the disclosed method to prime strand displacement replication of a nucleic acid molecule flanked by the ALTRs. ALTRs are preferably produced by rolling circle replication of a single-stranded, circular DNA molecule referred to as a terminal repeat circle. The sequence of the repeat unit in an ALTR is the same as the sequence in the terminal repeat circle used to make the ALTR.

The tail sequence of an ALTR provides an end that can be coupled to the end of a nucleic acid molecule of interest. Preferably, the tail sequence includes one or more restriction enzyme sites that can be cleaved to allow directed ligation of the ALTR to the end of a nucleic acid molecule. The tail sequence appears on only one end of the ALTR to facilitate flanking of nucleic acid molecules with ALTRs. The other end of the ALTR, which should not be capable of ligation to the nucleic acid molecule, will form the ends of the artificial long terminal repeat vector that results when a nucleic acid molecule is flanked by ALTRs.

An artificial long terminal repeat can include any desired number of repeat units. In general, the more repeat units present, the greater the level of amplification that will be obtained. There is no fundamental upper limit to the number of repeat units that an ALTR can have. It is preferred that an ALTR include from 7 to 50 repeat units. It is preferred that an ALTR include at least 50 repeat units. It is still more preferred that an ALTR include at least 100 repeat units. It is more preferred that an ALTR include at least 200 repeat units. It is more preferred that an ALTR include at least 300 repeat units. It is more preferred that an ALTR include at least 400 repeat units. It is most preferred that an ALTR include at least 600. Any combination of the preferred upper and lower limits for the number of primers in a set of primers described above are specifically contemplated, including all intermediate ranges.

ALTRs can also be made by direct synthesis or concatenation of repeat units. Direct synthesis is preferably accomplished by making two oligonucleotides where the 5' half of the first oligonucleotide is complementary to the 5' half of the second oligonucleotide, and the 3' half of the first oligonucleotide is complementary to the 3' half of the second oligonucleotide. This arrangement allows copies of the oligonucleotides to hybridize too each other in an overlapping chain that can be ligated to form a long, tandem repeat nucleic acid molecule.

F. DNA polymerases

DNA polymerases useful in the disclosed method must be capable of displacing, either alone or in combination with a compatible strand displacement factor, a hybridized strand encountered during replication. Such polymerases are referred to herein as strand displacement DNA polymerases. It is preferred that a strand displacement DNA polymerase lack a 5' to 3' exonuclease activity. Strand displacement is necessary to result in synthesis of multiple copies of a nucleic acid molecule. A 5' to 3' exonuclease activity, if present, might result in the destruction of a synthesized strand. It is also preferred that DNA polymerases for use in the disclosed method are highly processive. The suitability of a DNA polymerase for use in the disclosed method can be readily determined by assessing its ability to carry out strand displacement replication. Preferred strand displacement DNA polymerases are Bst large fragment DNA polymerase (Exo(−) Bst; Aliotta et al., *Genet. Anal.* (Netherlands) 12:185–195 (1996)) and exo(−)Bca DNA polymerase (Walker and Linn, *Clinical Chemistry* 42:1604–1608 (1996)). Other useful polymerases include bacteriophage φ29 DNA polymerase (U.S. Pat. Nos. 5,198,543 and 5,001,050 to Blanco et al.), phage M2 DNA polymerase (Matsumoto et al., *Gene* 84:247 (1989)), phage φPRD1 DNA polymerase (Jung et al., *Proc. Natl. Acad. Sci. USA* 84:8287 (1987)), exo(−)VENT® DNA polymerase (Kong et al., *J. Biol. Chem.* 268:1965–1975 (1993)), Klenow fragment of DNA polymerase I (Jacobsen et al., *Eur. J. Biochem.* 45:623–627 (1974)), T5 DNA polymerase (Chatterjee et al., *Gene* 97:13–19 (1991)), Sequenase (U.S. Biochemicals), PRD1 DNA polymerase (Zhu and Ito, *Biochim. Biophys. Acta.* 1219:267–276 (1994)), and T4 DNA polymerase holoenzyme (Kaboord and Benkovic, *Curr. Biol.* 5:149–157 (1995)). Exo(−)Bst DNA polymerase is most preferred.

Strand displacement can be facilitated through the use of a strand displacement factor, such as helicase. It is considered that any DNA polymerase that can perform strand displacement replication in the presence of a strand displacement factor is suitable for use in the disclosed method, even if the DNA polymerase does not perform strand displacement replication in the absence of such a factor. Strand displacement factors useful in strand displacement replication include BMRF1 polymerase accessory subunit (Tsurumi et al., *J. Virology* 67(12):7648–7653 (1993)), adenovirus DNA-binding protein (Zijderveld and van der Vliet, *J. Virology* 68(2):1158–1164 (1994)), herpes simplex viral protein ICP8 (Boehmer and Lehman, *J. Virology* 67(2):711–715 (1993); Skaliter and Lehman, *Proc. Natl. Acad. Sci. USA* 91(22):10665–10669 (1994)); single-stranded DNA binding proteins (SSB; Rigler and Romano, *J. Biol. Chem.* 270:8910–8919 (1995)); phage T4 gene 32 protein (Villemain and Giedroc, *Biochemistry* 35:14395–14404 (1996); and calf thymus helicase (Siegel et al., *J. Biol. Chem.* 267:13629–13635 (1992)).

A useful assay for selecting a polymerase is the primer-block assay described in Kong et al., *J. Biol. Chem.* 268:1965–1975 (1993). The assay consists of a primer extension assay using an M13 ssDNA template in the presence or absence of an oligonucleotide that is hybridized upstream of the extending primer to block its progress. Enzymes able to displace the blocking primer in this assay are useful for the disclosed method.

G. DNA ligases

Any DNA ligase is suitable for use in the disclosed method. Preferred ligases are those that preferentially form phosphodiester bonds at nicks in double-stranded DNA. That is, ligases that fail to ligate the free ends of single-stranded DNA at a significant rate are preferred. Thermostable ligases are especially preferred. Many suitable ligases are known, such as T4 DNA ligase (Davis et al., *Advanced Bacterial Genetics—A Manual for Genetic Engineering* (Cold Spring Harbor Laboratory, Cold Spring Harbor, N.Y., 1980)), *E. coli* DNA ligase (Panasnko et al., *J. Biol. Chem.* 253:4590–4592 (1978)), AMPLIGASE® (Kalin et al., *Mutat. Res.*, 283(2):119–123 (1992); Winn-Deen et al., *Mol Cell Probes* (England) 7(3):179–186 (1993)), Taq DNA ligase (Barany, *Proc. Natl. Acad. Sci. USA* 88:189–193 (1991), *Thermus thermophilus* DNA ligase (Abbott Laboratories), *Thermus scotoductus* DNA ligase and *Rhodothermus marinus* DNA ligase (Thorbjamardottir et al., *Gene* 151:177–180 (1995)). T4 DNA ligase is preferred for ligations involving RNA target sequences due to its ability to ligate DNA ends involved in DNA:RNA hybrids (Hsuih et al., *Quantitative detection of HCV RNA using novel ligation-dependent polymerase chain reaction*, American Association for the Study of Liver Diseases (Chicago, Ill, Nov. 3–7, 1995)).

H. Detection Labels

To aid in detection and quantitation of nucleic acids amplified using the disclosed method, detection labels can be directly incorporated into amplified nucleic acids or can be coupled to detection molecules. As used herein, a detection label is any molecule that can be associated with amplified nucleic acid, directly or indirectly, and which results in a measurable, detectable signal, either directly or indirectly. Many such labels for incorporation into nucleic acids or coupling to nucleic acid probes are known to those of skill in the art. Examples of detection labels suitable for use in the disclosed method are radioactive isotopes, fluorescent molecules, phosphorescent molecules, enzymes, antibodies, and ligands.

Examples of suitable fluorescent labels include fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7. Preferred fluorescent labels are fluorescein (5-carboxyfluorescein-N-hydroxysuccinimide ester) and rhodamine (5,6-tetramethyl rhodamine). Preferred fluorescent labels are FITC and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm; 672 nm), Cy5.5 (682 nm; 703 nm) and Cy7 (755 nm; 778 nm), thus allowing their simultaneous detection. The fluorescent labels can be obtained from a variety of commercial sources, including Molecular Probes, Eugene, Oreg. and Research Organics, Cleveland, Ohio.

Labeled nucleotides are a preferred form of detection label since they can be directly incorporated into the amplification products during synthesis. Examples of detection labels that can be incorporated into amplified DNA or RNA include nucleotide analogs such as BrdUrd (Hoy and Schimke, Mutation Research 290:217–230 (1993)), BrUTP (Wansick et al., *J. Cell Biology* 122:283–293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359–364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.*, 22:3226–3232 (1994)). A preferred nucleotide analog detection label for DNA is BrdUrd (BUDR triphosphate, Sigma), and a preferred nucleotide analog detection label for RNA is Biotin-16-uridine-5'-triphosphate (Biotin-16-dUTP, Boehringer Mannheim). Fluorescein, Cy3, and Cy5 can be linked to dUTP for direct labelling. Cy3.5 and Cy7 are available as avidin or anti-digoxygenin conjugates for secondary detection of biotin- or digoxygenin-labelled probes.

Detection labels that are incorporated into amplified nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo [3.3.1.1$^{3,7}$]decane]-4-yl)phenyl phosphate; Tropix, Inc.).

A preferred detection label for use in detection of amplified RNA is acridinium-ester-labeled DNA probe (GenProbe, Inc., as described by Arnold et al., *Clinical Chemistry* 35:1588–1594 (1989)). An acridinium-ester-labeled detection probe permits the detection of amplified RNA without washing because unhybridized probe can be destroyed with alkali (Arnold et al. (1989)).

Molecules that combine two or more of these detection labels are also considered detection labels. Any of the known detection labels can be used with the disclosed probes, tags, and method to label and detect nucleic acid amplified using the disclosed method. Methods for detecting and measuring signals generated by detection labels are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. As used herein, detection molecules are molecules which interact with amplified nucleic acid and to which one or more detection labels are coupled.

I. Oligonucleotide synthesis

Primers, terminal repeat circles, and any other oligonucleotides can be synthesized using established oligonucleotide synthesis methods. Methods to produce or synthesize oligonucleotides are well known in the art. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., *Ann. Rev. Biochem.* 53:323–356 (1984), (phosphotriester and phosphite-triester methods), and Narang et al., *Methods Enzymol.*, 65:610–620 (1980), (phosphotriester method). Protein nucleic acid molecules can be made using known methods such as those described by Nielsen et al., *Bioconjug Chem.* 5:3–7 (1994).

Many of the oligonucleotides described herein are designed to be complementary to certain portions of other oligonucleotides or nucleic acids such that stable hybrids can be formed between them. The stability of these hybrids can be calculated using known methods such as those described in Lesnick and Freier, *Biochemistry* 34:10807–10815 (1995), McGraw et al., *Biotechniques* 8:674–678 (1990), and Rychlik et al., *Nucleic Acids Res.* 18:6409–6412 (1990).

The materials described above can be packaged together in any suitable combination as a kit useful for performing the disclosed method.

II. Method

The disclosed method is based on strand displacement replication of nucleic acid sequences by multiple primers. The disclosed method generally involves attachment of artificial long terminal repeats (ALTRs) to a nucleic acid molecule and replication of the nucleic acid molecule primed by the primers that hybridize to the repeat sequence in the ALTR. During replication, the growing replicated strands displace other replicated strands from the nucleic acid molecule (or from another replicated strand) via strand displacement replication. As used herein, a replicated strand is a nucleic acid strand resulting from elongation of a primer hybridized to a nucleic acid molecule or to another replicated strand. Strand displacement replication refers to DNA replication where a growing end of a replicated strand encounters and displaces another strand from the template strand (or from another replicated strand). Displacement of replicated strands by other replicated strands is a hallmark of the disclosed method which allows multiple copies of a nucleic acid molecule to be made in a single, isothermic reaction.

A. Production of Artificial Long Terminal Repeats

ALTRs are preferably produced by rolling circle replication of a single-stranded, circular DNA molecule referred to as a terminal repeat circle. Rolling circle replication requires the use of two reagents: (a) a rolling circle replication primer, which is complementary to the primer complement portion of the terminal repeat circle, and (b) a strand displacement DNA polymerase. The DNA polymerase catalyzes primer extension and strand displacement in a processive rolling circle polymerization reaction that proceeds as long as desired, generating a molecule of up to 100,000 nucleotides or larger. The product of rolling circle replication is a single-stranded artificial long terminal repeat. The sequence of the repeat unit in an ALTR is the same as the sequence in the terminal repeat circle used to make the ALTR. The number of repeat units in the ALTR is determined by the size of the repeat unit, the rate of replication, and the amount of time the reaction is run.

To efficiently attach the ALTR to nucleic acid molecules, the single-stranded ALTR should be converted to a double-stranded ALTR, in whole or in part. The single-stranded ALTR that results from rolling circle replication can be made double-stranded in a variety of ways. Preferably, the single-stranded artificial long terminal repeat can be made double-stranded by performing the rolling circle replication in the presence of helicase, primase, ligase, and single-stranded DNA binding protein. These are the components necessary for lagging strand synthesis in DNA replication (Lee et al., *Molecular Cell* 1:1001–1010 (1998)). As the ALTR strand is synthesized during rolling circle replication, the primase primes lagging strand synthesis, the DNA polymerase extends the lagging strand, and ligase ligates the adjacent Okazaki fragments together. For this means of synthesis for the second strand of the ALTR, the repeat units (and thus also the terminal repeat circle) should contain a priming sequence recognized by the primase (Lee et al.). Preferably, the synthesis of the ALTR occurs in 2 minutes, and is stopped by the addition of a mixture of ddNTPs. The reaction is then incubated for another 30 minutes in the presence of ligase to complete the ligation of the Okazaki fragments.

The artificial long terminal repeat can also made double-stranded by ligating together oligonucleotides hybridized to the single-stranded artificial long terminal repeat strand made during the rolling circle replication. For this purpose, linear oligonucleotides of the same length and sequence as the terminal repeat circle are preferred. Shorter oligonucleotide (matching part of the sequence of the terminal repeat circle) can also be used, with the gaps between the hybridized oligonucleotides filled in with DNA polymerase (and the nicks ligated). The tail sequence of an ALTR can be designed to leave a convenient cohesive end to allow direct ligation of the ALTR to a nucleic acid molecule. Alternatively, the oligonucleotide can be designed to produce a sufficient double-stranded region to allow digestion with an appropriate restriction enzyme.

ALTRs can also be made by direct synthesis or concatenation of repeat units. Direct synthesis is preferably accomplished by making two oligonucleotides where the 5' half of the first oligonucleotide is complementary to the 5' half of the second oligonucleotide, and the 3' half of the first oligonucleotide is complementary to the 3' half of the second oligonucleotide. This arrangement allows copies of the oligonucleotides to hybridize too each other in an overlapping chain that can be ligated to form a long, tandem repeat nucleic acid molecule.

B. Ligation of Artificial Long Terminal Repeats to Nucleic Acid Molecules

The tail sequence of an ALTR provides an end that can be coupled to the end of a nucleic acid molecule of interest. Preferably, the tail sequence includes one or more restriction enzyme sites that can be cleaved to allow directed ligation of the ALTR to the end of a nucleic acid molecule. The tail sequence appears on only one end of the ALTR to facilitate flanking of nucleic acid molecules with ALTRs. The other end of the ALTR, which should not be capable of ligation to the nucleic acid molecule, will form the ends of the artificial long terminal repeat vector that results when a nucleic acid molecule is flanked by ALTRs.

Numerous methods are known for preparing and inserting nucleic acid molecules into vectors and any of these can be used to prepare nucleic acid molecules for use in the disclosed method (see, for example, Sambrook et al., *Molecular Cloning. A Laboratory Manual*, 2nd Edition (Cold Spring Harbor Laboratory Press, Cold Spring Harbor, N.Y., 1989)).

Preferably, the nucleic acid molecule is prepared by generating cohesive ends (sticky ends) to facilitate attachment of the ALTR to the nucleic acid molecule. This can be accomplished, for example by cleaving a nucleic acid molecule of interest, or a nucleic acid sample, with a restriction enzyme, or by adding linkers to the ends of nucleic acid molecules of interest that have, or can be processed to have sticky ends. The ALTR should be cleaved to present a compatible cohesive end. One or both of the ends of the nucleic acid molecule can also be left blunt ended, although this is not preferred. The two ends of nucleic acid molecules to be used in the disclosed method can also be made different to allow directional ligation of different ALTRs. For example, the two ends can have different sticky ends, or have one sticky end and one blunt end.

When two different ALTRs are ligated on either side of a DNA insert, two different primers are required for amplification. Upon denaturation of the DNA strands with the two different ALTRs, the rate of DNA renaturation is slow because interactions are exclusively inter-molecular. By contrast, upon denaturation of the DNA strands bounded by the same ALTR, the rate of DNA renaturation is fast because interactions are intra-molecular. Thus, inserts bounded by two different ALTRs should be replicated more efficiently than inserts bounded by identical ALTRs, due to the greater availability of single-stranded repeats in the first case.

For cloning with indexed artificial long terminal repeats, the nucleic acid molecules should be prepared by cleavage with a restriction enzyme having an interrupted palindrome or a cleavage site that is offset from the recognition sequence. Preferred restriction enzymes having an interrupted palindrome are type II restriction enzymes having degeneracy in the recognition/cleavage sequence around the site of cleavage. Preferred restriction enzymes having a cleavage site that is offset from the recognition sequence are type IIS restriction enzymes. These restriction enzymes will produce nucleic acid molecules having a distribution of sequences represented in their cohesive ends. This allows ligation of different indexed ALTRs depending on the actual sequence of the cohesive ends present on a given nucleic acid molecule.

An example of the central portion of an assembled ALTR vector is depicted below. The left side ALTR uses repeat A which hybridizes to primer A. The right side ALTR uses repeat B which hybridizes to primer B.

Repeat A (34 bases) (SEQ ID NO: 4)
ACGCAGCTCGTGTAATACGACTCGCATGCCTCCC
Primer A (22 bases) (SEQ ID NO: 5)
CGCAGCTCGTGTAATACGACTC
Repeat B (34 bases) (SEQ ID NO: 6)
ATGCATGCTCAGTGGTGCTGAGTAACAGCCTGGG
Primer B (22 bases) (SEQ ID NO: 7)
GGCTGTTACTCAGCACCACTGA Left side of ALTR vector (SEQ ID NO:8) with primers aligned (two repeats shown). NNNNNNN represents insert and polylinker sequences.

```
5'ACGCAGCTCGTGTAATACGCATCGCATGCCT
   |||||||||||||||||||||||||||||||
3'TGCGTCGAGCACATTATGCTGAGCGTACGGA
   |||||||||||||||||||||||||||
      5'-CGCAGCTCGTGTAATACGACTC>>>
   CCCACGCAGCTCGTGTAATACGACTCGCATGCCTCCCNNNNNNN...
   ||||||||||||||||||||||||||||||||||||||||||||
   GGGTGCGTCGAGCACATTATGCTGAGCGTACGGAGGGNNNNNNN...
      ||||||||||||||||||||||
      5'-CGCAGCTCGTGTAATACGACTC>>>
```

Right side of ALTR vector (SEQ ID NO:9) with primers aligned (two repeats shown). NNNNNNN represents insert and polylinker sequences.

```
        <<<AGTCACCACGACTCATTGTCGG-5'
           ||||||||||||||||||||||
...NNNNNNNGGGATGCATGCTCAGTGGTGCTGAGTAACAGCCTGGGAT
   ||||||||||||||||||||||||||||||||||||||||||||
...NNNNNNNCCCTACGTACGAGTCACCACGACTCATTGTCGGACCCTA
        <<<AGTCACCACGACTCATTGTCGG-5'
           ||||||||||||||||||||||
           GCATGCTCAGTGGTGCTGAGTAACAGCCT-3'
           |||||||||||||||||||||||||||||
           CGTACGAGTCACCACGACTCATTGTCGGA-5'
```

C. Strand Displacement Replication

The ALTR vector is amplified by strand displacement replication. In the disclosed method, multiple strand displacement primers hybridize to the primer complement portions of the repeat units in the ALTR. DNA replication initiated at the sites in the ALTR vector where the primers hybridize will extend to and displace strands being replicated from primers hybridized at adjacent sites. Displacement of an adjacent strand makes it available for hybridization to another primer and subsequent initiation of another round of replication. Amplification proceeds by replication initiated at each strand displacement primer and continuing through the nucleic acid molecule. A key feature of this method is the displacement of intervening primers during replication. Once the nucleic acid strands elongated from the right ALTR reaches the left ALTR, and vice versa, another round of priming and replication will take place. This allows multiple copies of a nested set of the target nucleic acid sequence to be synthesized in a short period of time. Strand displacement replication is preferably accomplished by using a strand displacing DNA polymerase or a DNA polymerase in combination with a compatible strand displacement factor.

Figure 3:
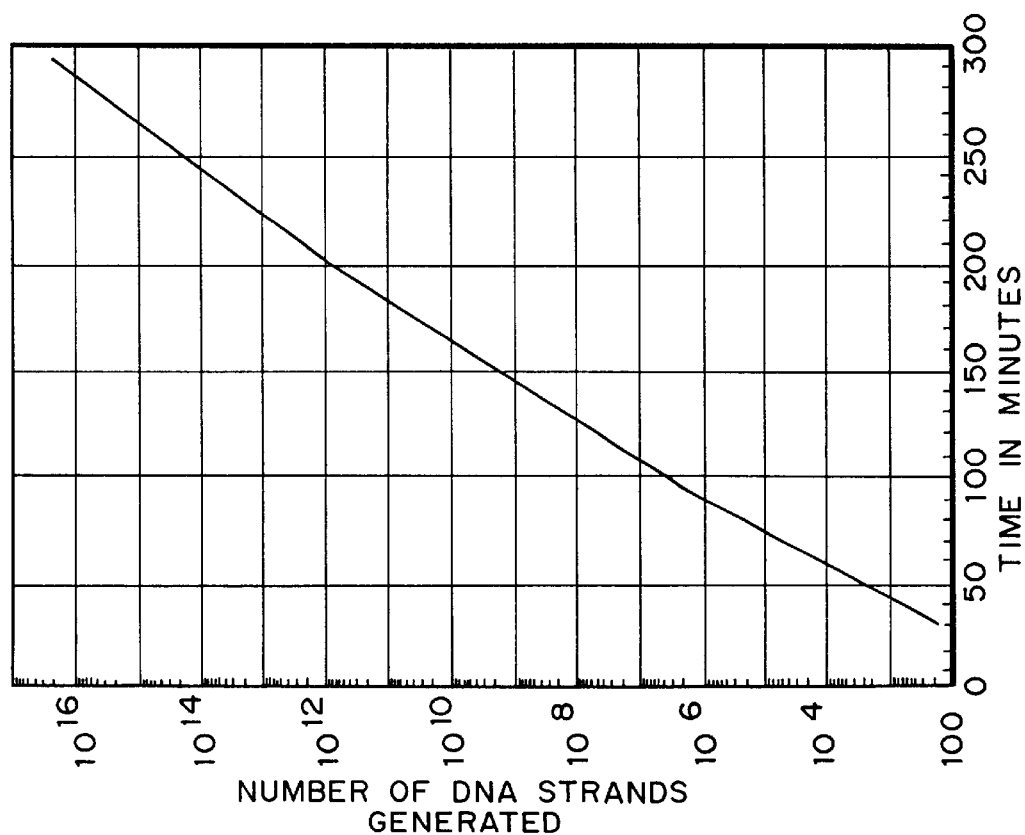
FIG. 3 is a graph of the number of DNA strands generated in the disclosed method versus time when amplifying a 14,000 bp insert using 600 repeat ALTRs.

By using a sufficient number of repeat units in the ALTRs, only a few rounds of replication are required to produce hundreds of thousands of copies of the nucleic acid sequence of interest. Examples of possible yields are shown in FIGS. 3 and 4. The disclosed method has advantages over the polymerase chain reaction since it can be carried out under isothermal conditions. No thermal cycling is needed because the polymerase at the head of an elongating strand (or a compatible strand-displacement factor) will displace, and thereby make available for hybridization, the strand ahead of it. Other advantages of strand displacement replication include the ability to amplify very long nucleic acid segments (on the order of 80 kilobases) and rapid amplification of shorter segments (10 kilobases or less). Long nucleic acid segments can be amplified in the disclosed method since there no cycling which could interrupt continuous synthesis or allow the formation of artifacts due to rehybridization of replicated strands. In strand displacement replication, single priming events at unintended sites will not lead to artifactual amplification at these sites (since amplification at the intended site will quickly outstrip the single strand replication at the unintended site).

Illustrations

The disclosed method can be further appreciated by reference to the following illustrations of examples of the disclosed method.

Illustration 1: The disclosed method (as applied to human genomic DNA derived from a preparation of purified chromosomal DNA) can be performed as follows.

1. Human DNA isolated from a pure preparation of a specific human chromosome (prepared by flow cytometry). The chromosomal DNA is fragmented by partial digestion with either MboI or Sau3AI, and the material is size-fractionated as described by Strong et al. (Nucleic Acids Res., 1997, Vol 25:3959–3961) to yield a DNA fraction in the size range of 55 to 75 kb.

2. Artificial long terminal repeats, containing a restriction enzyme sticky end, and 32 to 64 tandemly repeated sequences of approximately 110 bases, are generated by linear rolling circle replication, as shown in FIG. 1. The 32 to 64 repeated sequences are designed to serve as specific priming sites for strand displacement replication in a subsequent step (step 5, below) of the method.

3. The DNA is mixed with a 2.5:1 excess of artificial long terminal repeats, and the mixture is ligated to obtain DNA fragments bounded by two ALTRs (FIG. 2).

4. Unligated ALTRs are removed by preparative pulsed-field gel electrophoresis.

5. The DNA is mixed with a single strand displacement primer, complementary to the 32–64 repeats of the ALTRs. The mixture is diluted to terminal dilution, such that each well of a microtiter well contains either one or zero molecules of DNA (approximately 30% wells with zero molecules). One may use 20 microtiter dishes of 384 wells for a total of 7680 amplification reactions. The material is incubated with a DNA polymerase capable of supporting strand displacement replication, such as Sequenase (mixed with *E. Coli* SSB) or Bst Large fragment DNA polymerase. The reaction is incubated for a sufficient time (approximately 8 hours) to copy each single DNA molecule 100 million fold or more. FIGS. 3 and 4 show theoretical kinetics of DNA amplification for 65 kb DNA inserts in an artificial long terminal repeat vector, modeled using Mathematica 3.0.

6. The DNA generated in each well is isolated and analyzed by restriction enzyme digestion or sequencing.

Illustration 2: The disclosed method using indexed ALTRs can be performed as follows.

1. Human DNA isolated from a pure preparation of a specific human chromosome (prepared by flow cytometry). The chromosomal DNA is then digested with an interrupted palindrome enzyme such as SfiI (or an infrequent-cutter class IIS enzyme). The SfiI digest will ideally generate, on the average, 2000 fragments of approximately 40,000 to 95,000 bases each (average size, 65 kb). The fragments may contain any of a possible 64 sticky end sequences.

2. A set of 64 different indexed ALTRs is synthesized, where each indexed ALTR consists of a cohesive SfiI end (3 bases), joined to a sequence of approximately 5000 bases of dsDNA that will serve (after DNA denaturation) as a multiple priming domain. Each multiple priming domain comprises 32 to 50 priming sites of 20 bases plus 90 spacer bases. The tandem sequence thus contains 32 to 50 identical repeats of 110 bases (90+20), whose sequence is uniquely related to one specific cohesive end. In other words, for each cohesive end there is a specific cohesive partner sequence, and an associated tandem priming domain. One or two universal strand displacement primers are used in step 5 below to amplify any sequence bounded by any two indexed ALTRs.

3. The DNA digest is separated in 2016 aliquots, to each of which is added a mixture that contains only one combination of two (out of a possible 64×63/2=2016 different specific combinations) indexed ALTRs. The material is then ligated (FIG. 2) to join each combination of two indexer-linkers (more specifically, those which find cohesive partners) to any existing cognate cohesive ends in the chromosomal DNA digest. This procedure can be performed using 6 microtiter dishes of 384 wells. The indexed ALTRs are thus ligated at both termini of each competent DNA fragment (a DNA fragment with perfectly complementary 3-base sticky ends at both termini). Most combinations of 2 indexed ALTRs yield only one (or less frequently two or three) functional (amplifiable) ligated pairs joined to specific DNA fragments, because the number of different chromosomal DNA fragments is approximately 2000 while the number of possible indexed ALTR combinations is 2016.

4. The DNA is purified by QIAEX II (Qiagen, Inc.) to remove the excess of indexed ALTRs, resulting in a preparation of DNA fragments with a linker at each end (these are ALTR vectors). This step may be performed in microtiter wells. An aliquot of the purified material is used for amplification.

5. One or two different universal strand displacement primers are added to each sample of ligated material, and the solution is incubated with a DNA polymerase capable of supporting strand displacement replication, such as Sequenase (mixed with *E. Coli* SSB) or Bst Large fragment DNA polymerase. The reaction is incubated for a sufficient time (approximately 6 to 7 hours) to copy each indexed DNA fragment approximately 5 to 10 million fold.

6. The DNA generated by strand displacement amplification is fractionated in an agarose gel using a pulsed-field apparatus, and stained with Sybr-Green I to detect bands of amplified material. This gels analysis step is especially useful for reactions where two or three different DNA fragments may be amplified (in most reactions only one fragment should be amplified).

7. Optionally, reactions that generate a multiplicity of bands because by chance more than one set of 2 indexers participated in an amplification reaction, may be repeated, starting with the original preparation of linker-DNA, using individual combinations of only 2 indexer primers (out of the possible 10 pairs). Bands comprising a pure amplified fragment, flanked by two unique indexers, are isolated from the pulsed-field agarose gel using QIAEX II (Qiagen, Inc.). Illustration 3: The disclosed method using two ALTRs and two primerscan be performed as follows.

1. Human DNA is isolated from a pure preparation of a specific human chromosome (prepared by flow cytometry). The chromosomal DNA is fragmented by partial digestion with a mixture of SpeI (sticky end sequence CTAG) and Xho I (sticky end sequence TCGA), and the material is size-fractionated as described by Strong et al., *Nucleic Acids Res.* 25:3959–3961 (1997), to yield a DNA fraction in the size range of 55 to 75 kb.

2. Artificial terminal repeats of two different types, containing two different restriction enzyme sticky ends (SpeI and XhoI), and 32 to 64 tandemly repeated sequences of approximately 40 bases, are generated by ligation of DNA linkers. For each type of sticky end, a different ALTR repeat is used, so that the resulting ALTRs will be different. The 32 to 64 repeated sequences in each of the two types of ALTR are designed to serve as specific priming sites for a strand displacement replication.

3. The DNA is mixed with a 2.5:1 excess of the two types of artificial long terminal repeats (ALTRs), and the mixture is ligated to obtain DNA fragments bounded by two ALTRs. Due to chance, some insets will be bounded by the same ALTRs, while others will be bounded by different ALTRs.

4. Unligated ALTRs are removed by preparative Pulsed-field Gel Electrophoresis.

5. The DNA is mixed with a two universal primers, complementary to the 32–64 repeats of each type of ALTR. The two primers are used at a final concentration of 2 μM each. The mixture is diluted to terminal dilution, such that each well of a microtiter dish contains either one or zero molecules of DNA (approximately 30% wells with zero molecules). One may use 20 microtiter dishes of 384 wells for a total of 7680 amplification reactions. The material is incubated with a DNA polymerase capable of supporting strand displacement replication, such as Bst Large fragment DNA polymerase. The reaction is incubated at 62° C. for a sufficient time (approximately 5 hours) to copy each single DNA molecule one million fold or more. The clones derived from molecules bounded by two different ALTRs are amplified more efficiently than those derived from molecules bounded by identical ALTRs.

6. The DNA generated in each well is isolated and analyzed by restriction enzyme digestion or sequencing.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

I claim:

1. A method of amplifying a target nucleic acid sequence, the method comprising:

(a) replicating a terminal repeat circle by rolling circle replication primed by a rolling circle replication primer to form an artificial long terminal repeat, (b) ligating the artificial long terminal repeat to the ends of a target nucleic acid sequence to form an artificial long terminal repeat vector, (c) amplifying the artificial long terminal repeat vector by strand displacement replication primed by one or more strand displacement primers, wherein the target nucleic acid sequence is amplified.

2. The method of claim 1 wherein the amplification of the artificial long terminal repeat vector is primed by a single strand displacement primer.

3. A method of amplifying a target nucleic acid sequence, the method comprising:

(a) ligating artificial long terminal repeats to the ends of a target nucleic acid sequence to form an artificial long terminal repeat vector, (b) amplifying the artificial long terminal repeat vector by strand displacement replication primed by one or more strand displacement primers, wherein the target nucleic acid sequence is amplified.

4. The method of claim 3 wherein the amplification of the artificial long terminal repeat vector is primed by a single strand displacement primer.

5. The method of claim 3 wherein the amplification is performed under substantially isothermic conditions.

6. The method of claim 3 wherein the amplification does not involve thermal cycling.

7. The method of claim 3 wherein step (b) does not include thermal cycling.

8. The method of claim 3 wherein the artificial long terminal repeats each have at least five repeat units.

9. The method of claim 7 wherein the artificial long terminal repeats each have at least 25 repeat units.

10. The method of claim 3 wherein the artificial long terminal repeat is produced by replicating a terminal repeat circle by rolling circle replication primed by a rolling circle replication primer.

11. The method of claim 10 wherein the artificial long terminal repeat is made double-stranded by performing the rolling circle replication in the presence of helicase, primase, ligase, and single-stranded DNA binding protein.

12. The method of claim 10 wherein the artificial long terminal repeat is made double-stranded by ligating together oligonucleotides hybridized to the artificial long terminal repeat strand made during the rolling circle replication.

13. A method of amplifying nucleic acid molecules, the method comprising:
(a) digesting a nucleic acid sample with a type II restriction endonuclease having an interrupted palindrome recognition sequence or a type IIS restriction enzyme to produce nucleic acid molecules with cohesive ends,
(b) ligating artificial long terminal repeats to the ends of the nucleic acid molecules to form artificial long terminal repeat vectors,
(c) amplifying the artificial long terminal repeat vectors by strand displacement replication primed by one or more strand displacement primers,
wherein the nucleic acid molecule is amplified.

14. The method of claim 13 wherein the amplification of the artificial long terminal repeat vector is primed by a single strand displacement primer.

15. The method of claim 13 wherein a set of artificial long terminal repeats is used in step (b), wherein each member of the set has a different cohesive end, and wherein the cohesive ends of the members of the set collectively include complements to all possible cohesive ends that can be generated by cleavage with the restriction endonuclease,
wherein the artificial long terminal repeat ligated on each end of the nucleic acid molecules depends on the sequences of the cohesive ends of each nucleic acid molecule.

16. The method of claim 15 wherein step (b) is performed as multiple separate reactions where each reaction has a different pair of artificial long terminal repeats.

17. The method of claim 13 wherein the nucleic acid sample is a sample of genomic nucleic acid.

18. A method of amplifying a target nucleic acid sequence, the method comprising:
(a) ligation of multiple identical repeat units to form an artificial long terminal repeat,
(b) ligating the artificial long terminal repeat to the ends of a target nucleic acid sequence to form an artificial long terminal repeat vector,
(c) amplifying the artificial long terminal repeat vector by strand displacement replication primed by one or more strand displacement primers,
wherein the target nucleic acid sequence is amplified.

19. The method of claim 18 wherein the amplification of the artificial long terminal repeat vector is primed by a single strand displacement primer.

20. A kit for amplifying a target nucleic acid sequence, the kit comprising
an artificial long terminal repeat, wherein the artificial long terminal repeat comprises tandem repeat units and a tail sequence at one end, and
a strand displacement primer, wherein the strand displacement primer is complementary to a sequence in, or straddling, the repeat units.

21. The kit of claim 20 further comprising a strand displacing DNA polymerase or a DNA polymerase and a compatible strand displacement factor.

22. A kit for amplifying a target nucleic acid sequence, the kit comprising
a repeat circle, wherein the repeat circle is a single-stranded circular DNA molecule,
a rolling circle replication primer comprising a sequence complementary to a sequence in the repeat circle, and a tail sequence, and
a strand displacement primer, wherein the strand displacement primer is complementary to a sequence in, or straddling, the repeat units.

23. The kit of claim 22 further comprising a strand displacing DNA polymerase or a DNA polymerase and a compatible strand displacement factor.

24. The kit of claim 23 further comprising helicase, primase, ligase, and single-stranded DNA binding protein.

25. The kit of claim 23 further comprising ligase and linear oligonucleotides matching the sequence of the repeat circle.

* * * * *